(12) United States Patent
Young et al.

(10) Patent No.: US 12,123,764 B2
(45) Date of Patent: Oct. 22, 2024

(54) SYSTEM FOR ADJUSTING THE FIRMNESS OF A SUBSTRATE

(71) Applicant: Sleep Number Corporation, Minneapolis, MN (US)

(72) Inventors: Steven Jay Young, Los Gatos, CA (US); Carl Hewitt, San Jose, CA (US); Jonathan M. Olson, San Jose, CA (US); Alan Luckow, Ben Lomond, CA (US); Robert Dobkin, Monte Sereno, CA (US)

(73) Assignee: Sleep Number Corporation, Minneapolis, MN (US)

( * ) Notice: Subject to any disclaimer, the term of this patent is extended or adjusted under 35 U.S.C. 154(b) by 0 days.

(21) Appl. No.: 17/959,729

(22) Filed: Oct. 4, 2022

(65) Prior Publication Data
US 2023/0021928 A1    Jan. 26, 2023

Related U.S. Application Data

(63) Continuation of application No. 16/777,446, filed on Jan. 30, 2020, now abandoned.
(Continued)

(51) Int. Cl.
*A47C 19/22*    (2006.01)
*A47C 19/02*    (2006.01)
(Continued)

(52) U.S. Cl.
CPC ......... *G01G 19/445* (2013.01); *A47C 19/027* (2013.01); *A47C 19/22* (2013.01);
(Continued)

(58) Field of Classification Search
CPC ........ A47C 23/28; A47C 23/24; A61G 7/057; A61G 2203/34; A61G 5/1043
See application file for complete search history.

(56) References Cited

U.S. PATENT DOCUMENTS

| 411,343 A | * | 9/1889 | Leckron | A47C 23/28 5/261 |
|---|---|---|---|---|
| 2,990,899 A | | 7/1961 | De Bella | |

(Continued)

FOREIGN PATENT DOCUMENTS

| AU | 2012101423 | 10/2012 |
|---|---|---|
| DE | 2020/07019717 | 11/2016 |

(Continued)

OTHER PUBLICATIONS

Adami et al., "A Gaussian model for movement detection during sleep," Annu Int Cont IEEE Eng Med Biol Soc 2012, 2012:2263-6.
(Continued)

*Primary Examiner* — Adam C Ortiz
(74) *Attorney, Agent, or Firm* — Fish & Richardson P.C.

(57) ABSTRACT

A system for adjusting the firmness of a substrate configured to support a subject includes a first rod configured to be movable by a mechanism, a second rod parallel to and spaced from the first rod a distance that spans a majority of a dimension of the substrate, and flexible straps extending between the first rod and the second rod and attached to the first rod and the second rod at respective ends of each flexible strap. The mechanism is configured to move the first rod in a first direction to increase tension on the flexible straps and move the first rod in a second direction to decrease tension on the flexible straps. The mechanism can be manually operated by the subject or can be a motor that is controlled by a controller.

22 Claims, 10 Drawing Sheets

Related U.S. Application Data

(60) Provisional application No. 62/804,623, filed on Feb. 12, 2019.

(51) Int. Cl.
| | |
|---|---|
| *A61B 5/00* | (2006.01) |
| *A61B 5/0205* | (2006.01) |
| *A61B 5/11* | (2006.01) |
| *G01G 19/44* | (2006.01) |
| *G01G 19/52* | (2006.01) |
| *G01G 21/02* | (2006.01) |
| *G01V 9/00* | (2006.01) |
| *G05B 15/02* | (2006.01) |
| *G06N 5/04* | (2023.01) |
| *G06N 20/00* | (2019.01) |
| *G08B 21/22* | (2006.01) |
| *A61B 5/08* | (2006.01) |

(52) U.S. Cl.
CPC .......... *A61B 5/0205* (2013.01); *A61B 5/1102* (2013.01); *A61B 5/1115* (2013.01); *A61B 5/4818* (2013.01); *A61B 5/6891* (2013.01); *A61B 5/6892* (2013.01); *A61B 5/7203* (2013.01); *A61B 5/7246* (2013.01); *A61B 5/725* (2013.01); *A61B 5/7267* (2013.01); *A61B 5/7278* (2013.01); *A61B 5/7282* (2013.01); *A61B 5/7415* (2013.01); *G01G 19/52* (2013.01); *G01G 21/02* (2013.01); *G01V 9/00* (2013.01); *G05B 15/02* (2013.01); *G06N 5/04* (2013.01); *G06N 20/00* (2019.01); *G08B 21/22* (2013.01); *A61B 5/0816* (2013.01); *A61B 2560/0223* (2013.01)

(56) References Cited

U.S. PATENT DOCUMENTS

| | | | |
|---|---|---|---|
| 3,287,745 A | 11/1966 | Maddox | |
| 3,338,323 A | 8/1967 | Swersey | |
| 3,360,032 A | 12/1967 | Potter | |
| 3,722,611 A | 3/1973 | Tirkkonen | |
| 4,023,633 A | 5/1977 | Swersey et al. | |
| 4,121,453 A | 10/1978 | Levin et al. | |
| 4,281,730 A | 8/1981 | Swersey et al. | |
| 4,551,882 A | 11/1985 | Swersey et al. | |
| 4,633,237 A | 12/1986 | Tucknott et al. | |
| 4,667,357 A * | 5/1987 | Fortune | A47C 23/0435 5/936 |
| 4,679,569 A | 7/1987 | Lee | |
| 4,793,428 A | 12/1988 | Swersey | |
| 4,974,692 A | 12/1990 | Carruth et al. | |
| 5,173,977 A | 12/1992 | Carruth et al. | |
| 5,184,112 A | 2/1993 | Gusakov | |
| 5,276,432 A | 1/1994 | Travis | |
| 5,393,935 A | 2/1995 | Hasty et al. | |
| 5,393,938 A | 2/1995 | Bumbalough | |
| 5,747,745 A | 5/1998 | Neuman | |
| 5,831,221 A | 11/1998 | Geringer | |
| 5,861,582 A | 1/1999 | Flanagan et al. | |
| 6,280,392 B1 | 8/2001 | Yoshimi et al. | |
| 6,639,157 B2 | 10/2003 | Sternberg | |
| 6,680,442 B1 | 1/2004 | Rynd et al. | |
| 6,761,683 B2 | 7/2004 | Gryn et al. | |
| 6,765,154 B2 | 7/2004 | Sternberg | |
| 6,822,571 B2 | 11/2004 | Conway | |
| 6,852,086 B2 | 2/2005 | Atlas | |
| 7,176,391 B2 | 2/2007 | Metz et al. | |
| 7,253,366 B2 | 8/2007 | Bhai | |
| 7,335,839 B2 | 2/2008 | Metz et al. | |
| 7,437,787 B2 | 10/2008 | Bhai | |
| 7,467,426 B1 * | 12/2008 | Jarmon | A47C 23/28 5/88.1 |
| 8,048,005 B2 | 11/2011 | Dixon et al. | |
| 8,262,582 B2 | 9/2012 | Kortelainen | |
| 8,279,057 B2 | 10/2012 | Hirose | |
| 8,376,964 B2 | 2/2013 | Park et al. | |
| 8,444,558 B2 | 5/2013 | Young et al. | |
| 8,469,884 B2 | 6/2013 | David et al. | |
| 8,491,490 B2 | 7/2013 | Ozaki et al. | |
| 8,544,347 B1 | 10/2013 | Berme | |
| 8,672,853 B2 | 3/2014 | Young | |
| 8,821,418 B2 | 9/2014 | Meger et al. | |
| 8,984,687 B2 | 3/2015 | Stusynski et al. | |
| 9,013,313 B2 | 4/2015 | Paine | |
| 9,370,457 B2 | 6/2016 | Nunn et al. | |
| 9,383,251 B2 | 7/2016 | Dixon et al. | |
| 9,392,879 B2 | 7/2016 | Nunn et al. | |
| 9,445,751 B2 | 9/2016 | Young et al. | |
| 9,504,416 B2 | 11/2016 | Young et al. | |
| 9,506,106 B2 | 11/2016 | Gough et al. | |
| 9,510,688 B2 | 12/2016 | Nunn et al. | |
| 9,596,998 B2 | 3/2017 | Muehlsteff et al. | |
| 9,635,953 B2 | 5/2017 | Nunn et al. | |
| 9,679,462 B1 | 6/2017 | Robertson | |
| 9,770,114 B2 | 9/2017 | Brosnan et al. | |
| 9,844,275 B2 | 12/2017 | Nunn et al. | |
| 9,931,085 B2 | 4/2018 | Young et al. | |
| D818,383 S | 5/2018 | Sato et al. | |
| 10,058,467 B2 | 8/2018 | Stusynski et al. | |
| 10,092,242 B2 | 10/2018 | Nunn et al. | |
| 10,149,549 B2 | 12/2018 | Erko et al. | |
| 10,182,661 B2 | 1/2019 | Nunn et al. | |
| 10,201,234 B2 | 2/2019 | Nunn et al. | |
| 10,206,590 B2 | 2/2019 | Meriheina | |
| 10,251,490 B2 | 4/2019 | Nunn et al. | |
| 10,342,358 B1 | 7/2019 | Palashewski et al. | |
| 10,413,233 B2 | 9/2019 | Meriheina | |
| 10,441,086 B2 | 10/2019 | Nunn et al. | |
| 10,441,087 B2 | 10/2019 | Karschnik et al. | |
| 10,448,749 B2 | 10/2019 | Palashewski et al. | |
| 10,492,969 B2 | 12/2019 | Stusynski et al. | |
| 10,632,032 B1 | 4/2020 | Stusynski et al. | |
| 10,646,050 B2 | 5/2020 | Nunn et al. | |
| 10,674,832 B2 | 6/2020 | Brosnan et al. | |
| 10,716,512 B2 | 7/2020 | Erko et al. | |
| 10,729,255 B2 | 8/2020 | Erko et al. | |
| 10,736,432 B2 | 8/2020 | Brosnan et al. | |
| 10,750,875 B2 | 8/2020 | Palashewski et al. | |
| 10,827,846 B2 | 11/2020 | Karschnik et al. | |
| 10,881,219 B2 | 1/2021 | Nunn et al. | |
| 10,957,335 B2 | 3/2021 | Demirli et al. | |
| 10,959,535 B2 | 3/2021 | Karschnik et al. | |
| D916,745 S | 4/2021 | Stusynski et al. | |
| 10,980,351 B2 | 4/2021 | Nunn et al. | |
| 11,096,849 B2 | 8/2021 | Stusynski et al. | |
| 11,122,909 B2 | 9/2021 | Palashewski et al. | |
| 11,160,683 B2 | 11/2021 | Nunn et al. | |
| 11,206,929 B2 | 12/2021 | Palashewski et al. | |
| D954,725 S | 6/2022 | Stusynski et al. | |
| D968,436 S | 11/2022 | Stusynski et al. | |
| D975,121 S | 1/2023 | Stusynski et al. | |
| D1,000,464 S | 10/2023 | Stusynski et al. | |
| D1,018,476 S | 3/2024 | Dixon et al. | |
| 2002/0023785 A1 | 2/2002 | Sternberg | |
| 2002/0070867 A1 | 6/2002 | Conway et al. | |
| 2003/0140714 A1 | 7/2003 | Barua et al. | |
| 2003/0233034 A1 | 12/2003 | Varri et al. | |
| 2006/0129047 A1 | 6/2006 | Ruotoistenmaki | |
| 2006/0175097 A1 | 8/2006 | Pirzada | |
| 2007/0161917 A1 | 7/2007 | Ozaki et al. | |
| 2007/0191742 A1 | 8/2007 | Park | |
| 2008/0077020 A1 | 3/2008 | Young et al. | |
| 2010/0170043 A1 | 7/2010 | Young et al. | |
| 2011/0004435 A1 | 1/2011 | Lindstrom et al. | |
| 2011/0144455 A1 | 6/2011 | Young et al. | |
| 2012/0078573 A1 | 3/2012 | Kazuno | |
| 2012/0184862 A1 | 7/2012 | Foo et al. | |
| 2013/0135137 A1 | 5/2013 | Mulder et al. | |
| 2013/0146371 A1 | 6/2013 | Shih | |
| 2013/0174345 A1 | 7/2013 | Leu et al. | |
| 2014/0069729 A1 | 3/2014 | Shih | |

(56) References Cited

U.S. PATENT DOCUMENTS

| | | | |
|---|---|---|---|
| 2014/0135635 A1 | 5/2014 | Vanderpohl | |
| 2014/0277822 A1 | 9/2014 | Nunn et al. | |
| 2014/0352060 A1 | 12/2014 | Hirose | |
| 2015/0101870 A1 | 4/2015 | Gough et al. | |
| 2015/0126818 A1 | 5/2015 | Fung et al. | |
| 2015/0157258 A1 | 6/2015 | Beattie et al. | |
| 2015/0238021 A1* | 8/2015 | Wassermann | A61G 7/005 5/616 |
| 2015/0320229 A1* | 11/2015 | Edling | B60N 2/7094 5/690 |
| 2016/0015184 A1 | 1/2016 | Nunn et al. | |
| 2016/0051156 A1 | 2/2016 | Kim | |
| 2016/0063846 A1 | 3/2016 | Lemire et al. | |
| 2016/0235367 A1 | 8/2016 | Kolar et al. | |
| 2016/0367039 A1 | 12/2016 | Young et al. | |
| 2017/0065220 A1 | 3/2017 | Young et al. | |
| 2017/0067774 A1 | 3/2017 | Gough | |
| 2017/0128001 A1 | 5/2017 | Torre et al. | |
| 2017/0143269 A1 | 5/2017 | Young et al. | |
| 2017/0160709 A1 | 6/2017 | Yang | |
| 2017/0312154 A1 | 11/2017 | Kubiak et al. | |
| 2018/0008168 A1 | 1/2018 | Pearlman | |
| 2018/0098900 A1 | 4/2018 | Sato et al. | |
| 2018/0132627 A1 | 5/2018 | Van Erlach | |
| 2019/0053761 A1 | 2/2019 | Torre et al. | |
| 2019/0069840 A1 | 3/2019 | Young et al. | |
| 2019/0200777 A1 | 7/2019 | Demirli et al. | |
| 2019/0201265 A1 | 7/2019 | Sayadi et al. | |
| 2019/0201266 A1 | 7/2019 | Sayadi et al. | |
| 2019/0201267 A1 | 7/2019 | Demirli et al. | |
| 2019/0201268 A1 | 7/2019 | Sayadi et al. | |
| 2019/0201270 A1 | 7/2019 | Sayadi et al. | |
| 2019/0201271 A1 | 7/2019 | Grey et al. | |
| 2019/0290147 A1 | 9/2019 | Persen | |
| 2019/0328146 A1 | 10/2019 | Palashewski et al. | |
| 2019/0328147 A1 | 10/2019 | Palashewski et al. | |
| 2020/0060558 A1 | 2/2020 | Aleksov | |
| 2020/0110194 A1 | 4/2020 | Young et al. | |
| 2020/0158560 A1 | 5/2020 | Khair | |
| 2020/0315367 A1 | 10/2020 | Demirli et al. | |
| 2020/0336010 A1 | 10/2020 | Holmvik et al. | |
| 2020/0337470 A1 | 10/2020 | Sayadi et al. | |
| 2020/0359807 A1 | 11/2020 | Brosnan et al. | |
| 2020/0367663 A1 | 11/2020 | Nunn et al. | |
| 2020/0405070 A1 | 12/2020 | Palashewski et al. | |
| 2020/0405240 A1 | 12/2020 | Palashewski et al. | |
| 2021/0000261 A1 | 1/2021 | Erko et al. | |
| 2021/0034989 A1 | 2/2021 | Palashewski et al. | |
| 2021/0045541 A1 | 2/2021 | Nunn et al. | |
| 2021/0068552 A1 | 3/2021 | Palashewski et al. | |
| 2021/0112992 A1 | 4/2021 | Nunn et al. | |
| 2021/0267380 A1 | 9/2021 | Stusynski | |
| 2021/0282570 A1 | 9/2021 | Karschnik et al. | |
| 2021/0289947 A1 | 9/2021 | Karschnik et al. | |
| 2021/0314405 A1 | 10/2021 | Demirli et al. | |
| 2021/0346218 A1 | 11/2021 | Stusynski et al. | |
| 2022/0000273 A1 | 1/2022 | Palashewski et al. | |
| 2022/0000654 A1 | 1/2022 | Nunn et al. | |
| 2022/0031220 A1 | 2/2022 | Guidoboni | |
| 2022/0225786 A1 | 7/2022 | Palashewski et al. | |
| 2022/0265059 A1 | 8/2022 | Palashewski et al. | |
| 2022/0305231 A1 | 9/2022 | Stusynski et al. | |
| 2022/0346565 A1 | 11/2022 | Karschnik et al. | |
| 2022/0354431 A1 | 11/2022 | Molina et al. | |
| 2022/0386947 A1 | 12/2022 | Molina et al. | |
| 2022/0395233 A1 | 12/2022 | Siyahjani et al. | |
| 2023/0018558 A1 | 1/2023 | Demirli et al. | |
| 2023/0035257 A1 | 2/2023 | Karschnik et al. | |
| 2023/0037482 A1 | 2/2023 | Demirli et al. | |
| 2023/0054736 A1 | 2/2023 | Holmvik et al. | |
| 2023/0063373 A1 | 3/2023 | Young et al. | |
| 2023/0142604 A1 | 5/2023 | Dixon et al. | |
| 2023/0148762 A1 | 5/2023 | Karschnik et al. | |
| 2023/0181104 A1 | 6/2023 | Johnston et al. | |
| 2023/0190199 A1 | 6/2023 | Molina | |
| 2023/0210256 A1 | 7/2023 | MacLachlan et al. | |
| 2023/0210268 A1 | 7/2023 | Kirk et al. | |
| 2023/0210269 A1 | 7/2023 | Hill et al. | |
| 2023/0210274 A1 | 7/2023 | Hill et al. | |
| 2023/0210275 A1 | 7/2023 | Hill et al. | |
| 2023/0218093 A1 | 7/2023 | Nunn et al. | |
| 2023/0255843 A1 | 8/2023 | Sayadi et al. | |
| 2023/0363963 A1 | 11/2023 | Sayadi et al. | |
| 2023/0380756 A1 | 11/2023 | Palashewski et al. | |
| 2023/0404282 A1 | 12/2023 | Sayadi et al. | |
| 2023/0404825 A1 | 12/2023 | Stusynski et al. | |
| 2023/0412683 A1 | 12/2023 | Demirli et al. | |
| 2024/0016302 A1 | 1/2024 | Brosnan et al. | |
| 2024/0032705 A1 | 2/2024 | Nunn et al. | |
| 2024/0041221 A1 | 2/2024 | Blomseth et al. | |
| 2024/0041677 A1 | 2/2024 | Grey et al. | |
| 2024/0091487 A1 | 3/2024 | Molina et al. | |
| 2024/0138579 A1 | 5/2024 | Karschnik et al. | |

FOREIGN PATENT DOCUMENTS

| | | |
|---|---|---|
| EP | 0218957 | 4/1987 |
| EP | 1635153 | 3/2008 |
| EP | 2805702 | 11/2014 |
| EP | 1937148 | 1/2015 |
| FI | 116097 | 9/2005 |
| GB | 2119528 | 11/1983 |
| JP | H07198224 | 3/1995 |
| JP | 2002-182270 | 6/2002 |
| JP | 2004-024370 | 1/2004 |
| JP | 4002905 | 11/2007 |
| JP | 2012-207798 | 10/2012 |
| JP | 2014-233485 | 12/2014 |
| JP | 2014-235090 | 12/2014 |
| KR | 20060092037 | 8/2006 |
| KR | 10-2011-0033102 | 3/2011 |
| KR | 10-2012-0045660 | 5/2012 |
| KR | 10-2012-0119684 | 10/2012 |
| KR | 20120119684 | 10/2012 |
| KR | 101798498 | 11/2017 |
| WO | WO 1999/017658 | 4/1999 |
| WO | WO 2007/042960 | 4/2007 |
| WO | WO 2011/009085 | 1/2011 |
| WO | WO 2013/181474 | 12/2013 |
| WO | WO 2015/008677 | 1/2015 |
| WO | WO 2015/089274 | 6/2015 |
| WO | WO 2017/199944 | 11/2017 |
| WO | WO 2018/079403 | 5/2018 |
| WO | WO 2020/102383 | 5/2020 |

OTHER PUBLICATIONS

Adami et al., "A method for classification of movements in bed," Annu Int Conf IEEE Eng Med Biol Soc 2011, 2011, 7881-4 (abstract only).

Adami et al., "A subject state detection approach to determine rest-activity patterns using load cells," Annu Int Cont IEEE Eng Med Biol Soc. 2010, 2010:204-7.

Adami et al., "A System for Unobtrusive Monitoring of Mobility in Bed," 2008 11th IEEE International Conference on Computational Science and Engineering—Workshops, San Paulo, 2008, pp. 13-18 (abstract only).

Adami et al., "Assessment and Classification of Movements in Bed Using Unobtrusive Sensors Dissertation," ProQuest Information and Learning Company, Aug. 2006, 24 pages.

Adami et al., "Comparison of load cells and wrist-actigraphy for unobtrusive monitoring of sleep movements," Annu Int Cont IEEE Eng Med Biol Soc. 2009, 2009:1314-7.

Adami et al., "Detection and Classification of Movements in Bed using Load Cells," Cont Proc IEEE Eng Med Biol Soc 2005, 2006:589-92 (abstract only).

Adami et al., "Detection of Movement in Bed Using Unobtrusive Load Cell Sensors," in IEEE Transactions on Information Technology in Biomedicine, Mar. 2010, vol. 14, No. 2, pp. 481-490 (abstract only).

(56) References Cited

OTHER PUBLICATIONS

Adami et al., "Unobtrusive monitoring of sleep patterns," Proceedings of the 25th Annual International Conference of the IEEE Engineering in Medicine and Biology Society (IEEE Cat. No.03CH37439), Cancun, 2003, vol. 2, pp. 1360-1363 (abstract only).
Adami et al., "Unobtrusive Movement Detection during Sleep based on Load Cell Dynamics, " 2013, 9 pages.
Adami et al., "Using load cells under the bed as a non-contact method for detecting periodic leg movements," 2014, IRBM. 35.10. 1016/j.irbm.2014, 1 page.
Alaziz et al., "Motion Scale: A Body Motion Monitoring System Using Bed-Mounted Wireless Load Cells," 2016 IEEE First International Conference on Connected Health: Applications, Systems and Engineering Technologies (CHASE), Washington, DC, 2016, pp. 183-192.
Alihanka et al., "A new method for long-term monitoring of the ballistocardiogram, heart rate, and respiration," American Journal of Physiology-Regulatory, Integrative and Comparative Physiology, 1981, R384-R392 (abstract only).
Alihanka et al., "A static charge sensitive bed. A new method for recording body movements during sleep," Electroencephalography and Clinical Neurophysiology, vol. 46, Issue 6, 1979, pp. 731-734 (abstract only).
Alivar et al., "Motion Detection in Bed-Based Ballistocardiogram to Quantify Sleep Quality," GLOBECOM 2017-2017 IEEE Global Communications Conference, Singapore, 2017, 6 pages.
Aung Aung et al., "Evaluation and analysis of multimodal sensors for developing in and around the bed patient monitoring system," 2010 Annual International Conference of the IEEE Engineering in Medicine and Biology, Buenos Aires, 2010, pp. 2159-2162 (abstract only).
Austin et al. "Unobtrusive classification of sleep and wakefulness using load cells under the bed," Annual International Conference of the IEEE Engineering in Medicine and Biology Society, IEEE Engineering in Medicine and Biology Society. Annual International Conference vol. 2012, 5254-7.
Beattie et al., "A time-frequency respiration tracking system using non-contact bed sensors with harmonic artifact rejection," Annu Int Cont IEEE Eng Med Biol Soc. 2015 Aug. 2015:8111-4.
Beattie et al., "Accurate scoring of the apnea-hypopnea index using a simple non-contact breathing sensor," J Sleep Res. Jun. 2013; 22(3):356-62.
Beattie et al., "Classification of Breathing Events Using Load Cells under the Bed," Cont Proc IEEE Eng Med Biol Soc. 2009, 2009: 3921-3924.
Beattie et al., "Classification of lying position using load cells under the bed," Annu Int Conf IEEE Eng Med Biol Soc. 2011, 2011:474-7.
Bio-Physical Signal, Advanced Biometric Research Center, Department of Biomedical Engineering, College of Medicine, Seoul National University, 2015, 4 pages <http://abrc.snu.ac.kr/korean/viewtopic.php?p=4039>.
Braunstein et al. "Design of a two-dimensional ballistocardiograph," The Journal of clinical investigation vol. 29.9 (1950): 1219-26.
Brink et al., "Contact-free measurement of heart rate, respiration rate, and body movements during sleep," Behavior Research Methods 38, 511-521 (2006).
Brotmacher, "The normal ballistocardiogram," Br Heart Journal, Apr. 1956, 18(2):145-52.
Carlson et al., "Bed-based instrumentation or unobtrusive sleep quality assessment in severely disabled autistic children," Annu Int Cont IEEE Eng Med Biol Soc, Aug. 2016, 2016:4909-4912 (abstract only).
Carlson, "Development of a bed-based nighttime monitoring toolset Dissertation," Kansas State University, May 2019, <https://krex.k-state.edu/dspace/handle/2097/39650>, 154 pages (abstract only).
Chamadiya et al., "Textile-Based, Contactless ECG Monitoring for Non-ICU Clinical Settings," Journal of Ambient Intelligence and Humanized Computing, Jul. 2012, 11 pages.

Choi et al., "Non-constraining sleep/wake monitoring system using bed actigraphy," Med Biol Eng Comput, Jan. 2007, 45(1):107-14 (abstract only).
Choi et al., "Slow-wave sleep estimation on a load-cell-installed bed: a non-constrained method," Physiol Meas, Nov. 2009, 30(11):1163-70 (abstract only).
Chung et al., "Noninvasive heart rate variability analysis using loadcell-installed bed during sleep," Annu Int Cont IEEE Eng Med Biol Soc. 2007, 2007:2357-60 (abstract only).
Chung et al., "Wakefulness estimation only using ballistocardiogram: nonintrusive method for sleep monitoring," Annu Int Cont IEEE Eng Med Biol Soc. 2010, 2010:2459-62.
Di Lecce et al., "Smart Postural Monitor for Elderly People," Jul. 2013, 4 pages.
Extended European Search Report in European Appln No. 19870848.9, dated Mar. 20, 2023, 13 pages.
Gordon, "Certain Molar Movements of the Human Body produced by the Circulation of the Blood," J Anal Physiol, 1877, 11(Pt 3):533-536.
International Search Report and Written Opinion of corresponding International Application No. PCT/US2019/055121; mailed Jan. 23, 2020, 11 pages.
Jung et al., "Estimation of sleep onset latency based on the blood pressure regulatory reflex mechanism.," IEEE J Biomed Health Inform, May 2013,17(3):534-44 (abstract only).
Jung et al., "Nocturnal Awakening and Sleep Efficiency Estimation Using Unobtrusively Measured Ballistocardiogram," IEEE Transactions on Biomedical Engineering, Jan. 2014, vol. 61, No. 1, pp. 131-138.
Kim et al., "Ballistocardiogram: Mechanism and Potential for Unobtrusive Cardiovascular Health Monitoring," Sci Rep 6, Aug. 2016, 6 pages.
Lee et al., "Ballistocardiogram of baby during sleep," Annu Int Conf IEEE Eng Med Biol Soc. 2015, 2015:7167-70 (abstract only).
Lee et al., Physiological Signal Monitoring Bed for Infants Based on Load-Cell Sensors, Sensors, 2016, 16,409, 19 pages.
Load Cell Central website, "Hospital Beds, Portable Carts, Table Load Cell System," <https://www.800loadcell.com/special-applications/other-specialized-systems/custom-load-cell-5.html, available on or before Nov. 2020, 3 pages.
Loadstar Sensors Website, "Monitor Sleep Patterns," https://www.loadstarsensors.com/monitor-sleep-patterns.html, accessed Nov. 2020, 1 page.
March, "Three-Plane Ballistocardiography: The Effect of Age on the Longitudinal, Lateral, and Dorsoventral Ballistocardiograms," Circulation. 1955, 12:869-882, 14 pages.
Mietus et al., "Detection of obstructive sleep apnea from cardiac interbeat interval time series," Computers in Cardiology 2000. vol. 27 (Cat. 00CH37163), Cambridge, MA, 2000, pp. 1753-1756.
Muller, Projekt NEMESIS Niederfrequente elektrische und magnetische Felder und Elektrosensibilitat in der Schweiz; Doctoral Thesis; 2000; ETH Zurich Research collection (English summary only).
Nagura et al., "A practical BCG measuring system with bed sensors and algorithm for heartbeat detection," 2018 IEEE 15th International Workshop on Advanced Motion Control (AMC), Tokyo, 2018, pp. 317-321 (abstract only).
Nagura et al., "An estimation of heart rate variability from ballistocardiogram measured with bed leg sensors," 2018 IEEE International Conference on Industrial Technology (ICIT), Lyon, 2018, pp. 2005-2009.
Nehmer el al., "The Intelligent Bed—Ambient Monitoring of Sick and Disabled Persons through the Use of Load Sensors in Bed Legs," ERCIM News 87, Oct. 13, 2011, pp. 26-27, https://ercim-news.ercim.eu/en87/special/thentelligent-bed.
Nihon Kohden [website], "History—1950's, product—MB-1 Ballistocardiograph," 1953, <https://www.nihonkohden.com/company/history/1950s.html>, available on or before Nov. 2020, 5 pages.
Noh et al., "BCG Monitoring System using Unconstrained Method with Daubechies Wavelet Transform," Inter. Cont. on IML 2009, pp. 338-344.
Nukaya et al., "Noninvasive Bed Sensing of Human Biosignals Via Piezoceramic Devices Sandwiched Between the Floor and Bed," IEEE Sensors Journal, Mar. 2012, 12(3), 8 pages.

(56) References Cited

OTHER PUBLICATIONS

Pinheiro et al., "Study on Ballistocardiogram Acquisition in a Moving Wheelchair with Embedded Sensors," Metrology and Measurement Systems, 2012, 739-750.
RICOH Website; Bed Sensor announced 2017; https://www.ricoh.com/about/empowering-digital-workplaces/articles/innovations-vital-to-enhancing-long-term-care; accessed Nov. 2020, 9 pages.
Rosales et al., "Heartbeat detection from a hydraulic bed sensor using a clustering approach," Annu Int Cont IEEE Eng Med Biol Soc. 2012;2012:2383-7 (abstract only).
Sadek et al., "Ballistocardiogram signal processing: a review," Health Inf Sci Syst 7, May 2019, 23 pages.
Schrempf et al., "Measuring nightly activity, body weight and body weight change rate with a sensor equipped bed," Annu Int Cont IEEE Eng Med Biol Soc. 2010;2010:2151-4 (abstract only).
Sensotech Website; Patient Monitoring Sensors—Load Cell for Bed Weighing; https://www.sensomaticloadcell.in/patient-monitoring-sensor.html; accessed Nov. 2020, 2 pages.
Shin et al., "Automatic ballistocardiogram (BCG) beat detection using a template matching approach," Annu Int Cont IEEE Eng Med Biol Soc. 2008, 2008:1144-6 (abstract only).
Starr et al., "Twenty-Year Studies with the Ballistocardiograph: The Relation between the Amplitude of the First Record of "Healthy" Adults and Eventual Mortality and Morbidity from Heart Disease," Circulation, 1961, 23:714-732.
Stryker Maintenance Manual, "MedSurge Bed Model 3002 S3 Patriot Series," Oct. 2008, retrieved from URL <https://techweb.stryker.com/MedSurg/3002S3/0806/maintenance/patriot/3006-009-102C.pdf>, 227 pages.
Su et al., "Ballistocardiogram Measurement System Using Three Load-Cell Sensors Platform in Chair," 2009 2nd International Conference on Biomedical Engineering and Informatics, Tianjin, 2009, pp. 1-4 (abstract only).
Talbot et al., "Dynamic Comparison of Current Ballistocardiographic Methods: Part I: Artefacts in the Dynamically Simple Ballistocardiographic Methods," Circulation. 1955, 12:577-587.
VPG Transducers, "Medical Beds," retrieved from <https://vpgtransducers.com/markets/medical>, accessed Nov. 2020, 3 pages.
Watanabe et al., "Ubiquitous Health Monitoring at Home—Sensing of Human Biosignals on Flooring, on Tatami Mat, in the Bathtub, and in the Lavatory," in IEEE Sensors Journal, vol. 9, No. 12, Dec. 2009, pp. 1847-1855.
Williams, "This 30-ppm Scale Proves that Analog Designs Aren't Dead Yet," Oct. 5, 1976, 4 pages.
U.S. Appl. No. 16/719,177, filed Dec. 18, 2019, Nunn et al.
U.S. Appl. No. 17/745,508, filed May 16, 2022, Nunn et al.
U.S. Appl. No. 18/389,388, filed Nov. 14, 2023, Johnston et al.
U.S. Appl. No. 18/404,647, filed Jan. 4, 2024, Palashewski et al.
U.S. Appl. No. 18/416,387, filed Jan. 18, 2024, Nunn et al.
U.S. Appl. No. 18/433,289, filed Feb. 5, 2024, Demirli et al.
U.S. Appl. No. 18/538,884, filed Dec. 13, 2023, Palashewski et al.
U.S. Appl. No. 18/602,407, filed Mar. 12, 2024, Holmvik et al.
U.S. Appl. No. 18/604,949, filed Mar. 14, 2024, Palashewski et al.
U.S. Appl. No. 18/639,292, filed Apr. 18, 2024, Mayandi et al.
U.S. Appl. No. 18/643,648, filed Apr. 23, 2024, Sohn et al.
U.S. Appl. No. 29/881,955, filed Jan. 9, 2023, Stusynski et al.
U.S. Appl. No. 29/910,800, filed Aug. 24, 2023, Stusynski et al.
U.S. Appl. No. 29/924,373, filed Jan. 18, 2024, Dixon et al.

\* cited by examiner

SYSTEM FOR ADJUSTING THE FIRMNESS OF A SUBSTRATE

CROSS-REFERENCE TO RELATED APPLICATION

This application is a continuation of U.S. patent application Ser. No. 16/777,446, filed Jan. 30, 2020, which claims priority to and the benefit of U.S. Provisional Application Patent Ser. No. 62/804,623, filed Feb. 12, 2019, the entire disclosure of which is hereby incorporated by reference.

TECHNICAL FIELD

This disclosure relates to systems for adjusting the firmness of a substrate configured to support a subject.

BACKGROUND

Substrates such as mattresses can be purchased with different levels of firmness. However, it can be difficult to understand what firmness would be best for a subject when the subject is shopping for a new mattress, particularly when shopping online. Even when technology is used to assess a subject's best firmness during the buying process, the selected firmness is not always ideal for the subject, and desired firmness may change with time or due to circumstances. Most substrates do not have the ability to adjust firmness in different areas of the substrate. Those that do typically use air bladders, which have their own drawbacks.

SUMMARY

Disclosed herein are implementations of systems for adjusting the firmness of a substrate configured to support a subject. These systems can be utilized with nearly any substrate. These systems can be manual, such that the subject manually selects the firmness he or she desires. These systems can be automatic, such that a controller adjusts the firmness of the substrate based on subject input and/or strain gauge or other sensor input. These systems can automatically adjust different sections of a substrate to provide uniform force against the substrate. Other advantages of these systems disclosed herein are contemplated.

As one example, a system for adjusting the firmness of a substrate configured to support a subject includes a first rod configured to be movable by a mechanism, a second rod parallel to and spaced from the first rod a distance that spans a majority of a dimension of the substrate, and flexible straps extending between the first rod and the second rod and attached to the first rod and the second rod at respective ends of each flexible or elastic strap. The mechanism is configured to move or rotate the first rod in a first direction to increase tension on the flexible straps and move the first rod in a second direction to decrease tension on the flexible straps. The mechanism can be manually operated by the subject to adjust the firmness to that desired by the subject.

As a non-limiting example, the mechanism can be a handle extending from the first rod to be accessible to the subject, the handle movable by the subject to turn the first rod in the first direction and turn the first rod in the second direction. The mechanism can include stops to hold the handle in a particular position, the particular position associated with a selected firmness.

Another example of a system for adjusting the firmness of a substrate configured to support a subject includes a motor, a controller configured to control the motor, a first rod configured to be moved by the motor, a second rod parallel to the first rod, the first rod and the second rod spaced to span a majority of a width of the substrate, and flexible straps extending between the first rod and the second rod and attached to the first rod and the second rod at respective ends of each flexible strap. The controller is configured to control the motor to move the first rod in a first direction to increase tension on the flexible straps and move the first rod in a second direction to decrease tension on the flexible straps.

Another example of a system for adjusting the firmness of a substrate configured to support a subject includes a pulley system comprising pulleys and a cable positioned around the pulleys. A motor is connected to one end of the cable and a strain gauge is positioned at the other end of the cable. The cable tension is controlled by the motor. A controller can control the motor to adjust the cable tension based on output from the strain gauge. Multiple pulley systems can be used under one substrate to selectively and individually change the firmness of different sections of the substrate, such as the head-supporting section, the mid-body-supporting section and the feet-supporting section.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Disclosed herein are implementations of systems for adjusting the firmness of a substrate configured to support a subject. These systems can be utilized with nearly any substrate. These systems can be manual, such that the subject manually selects the firmness he or she desires. These systems can be automatic, such that a controller adjusts the firmness of the substrate based on subject input and/or strain gauge input. These systems can automatically adjust different sections of a substrate to provide uniform force against the substrate.

Figure 1:
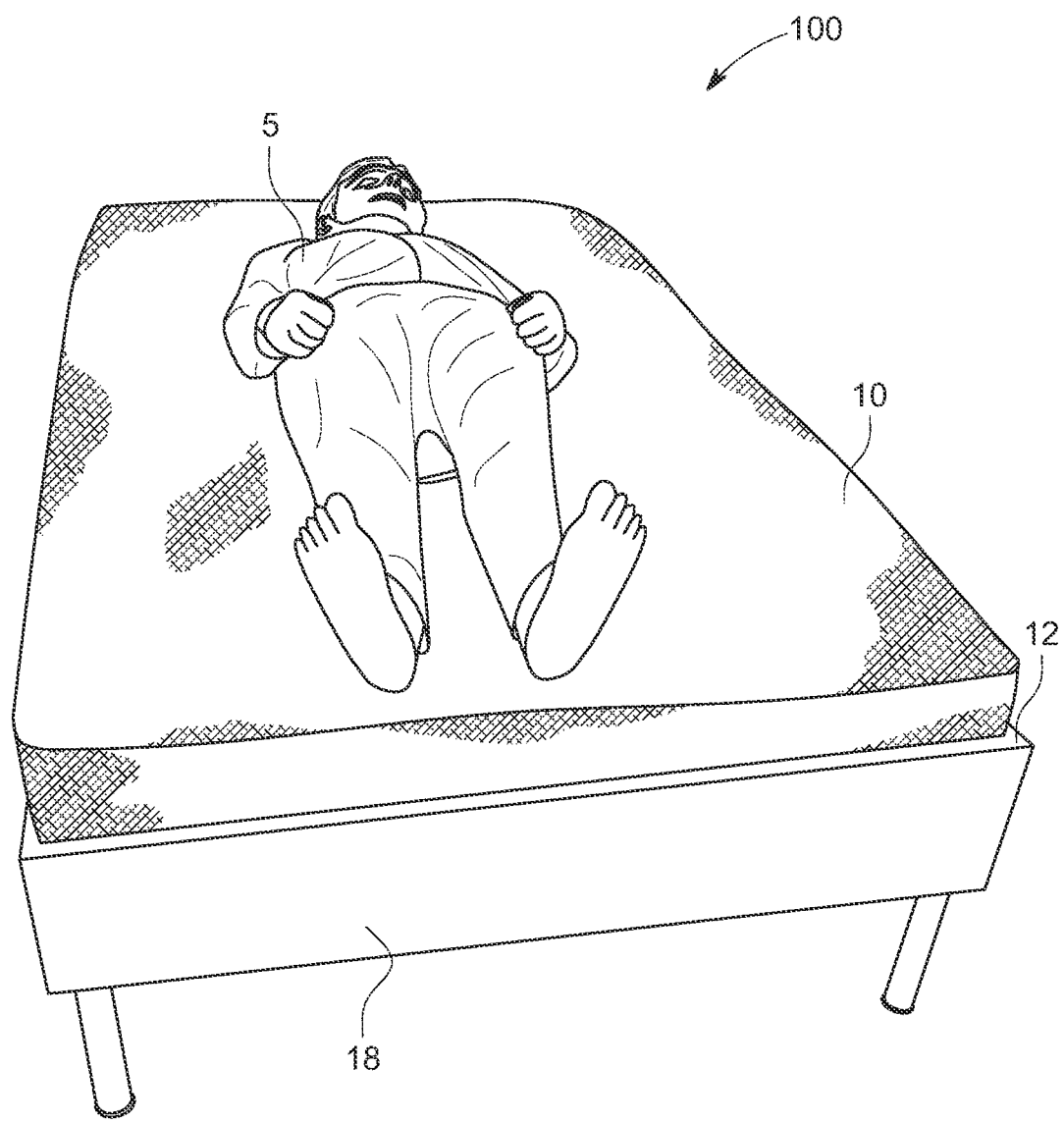
FIG. 1 is a perspective view of a subject lying on a substrate under which a system for adjusting the firmness of the substrate as disclosed herein is incorporated.
Figure 2:
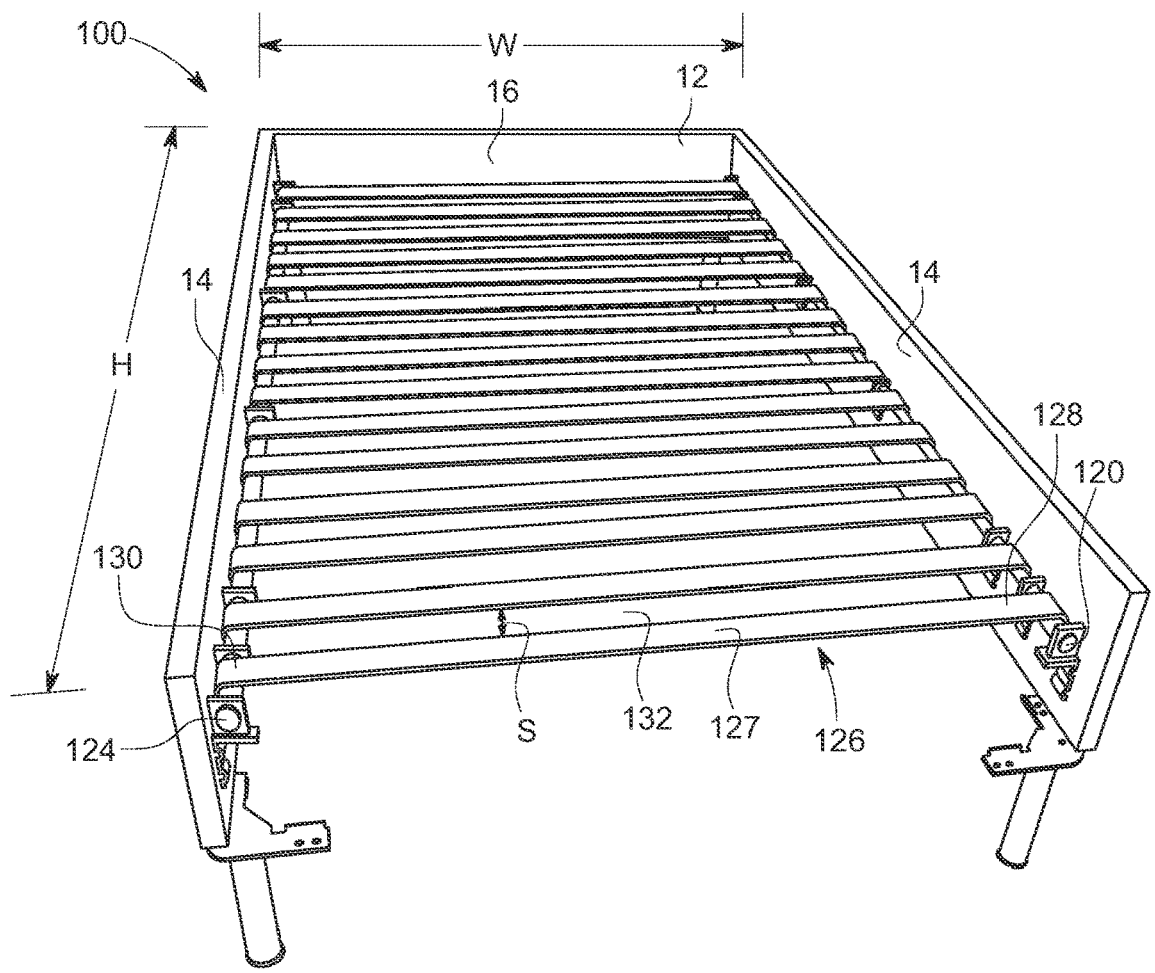
FIG. 2 is a perspective view of an embodiment of a system for adjusting the firmness of the substrate as disclosed herein.

As one example, a system for adjusting the firmness of a substrate configured to support a subject is illustrated in FIGS. 1-3. FIG. 1 illustrates a system 100 having a mattress as a substrate 10 supporting a subject 20. The substrate 10 is supported in a bed frame 12. FIG. 2 illustrates the system 100 when the substrate 10 is removed, exposing the system. The bed frame 12 illustrated is an example only. The bed frame 12 need not have side boards 14. The bed frame 12 may only have a head board 16. The bed frame 12 may be without side boards 14, a head board 16 and a foot board 18, i.e., it may only be a frame connected to bed legs to support the substrate off of the ground. It is noted that the footboard 18 in FIG. 2 is removed for illustration of the system 100.

The system 100 includes a first rod 120 configured to be movable by a mechanism 122, a second rod 124 parallel to and spaced from the first rod 120 a distance that spans a majority or all of a width W of the substrate 10 and/or bed frame 12. Although the movable rod 120 and the mechanism 122 are illustrated on the right side of the bed frame 12 with the second rod 124 on the left side, they can alternatively be on the other sides. Flexible straps 126 have a central portion 127 extending between the first rod 120 and the second rod 124 and attach to the first rod 120 and the second rod 124 at respective ends 128, 130 of each flexible strap 126, also referred to as first and second rod attachment portions 128, 130. The rods 120, 124 extend along the bed frame 12 in a head-to-toe direction H with respect to a subject 20 lying on the substrate 10. The rods 120, 124 can extend the entire length (in the head-to-toe direction H) of the substrate 10 and/or bed frame 12 or may extend along a portion of the length of the substrate 10 and/or bed frame 12. The greater the span of the rods, the more area of the substrate that the firmness can be controlled. Multiple flexible straps 126 are used so that when spaced along the parallel rods 120, 124, the flexible straps 126 extend along the entire length or a majority of the length of the rods 120, 124. The flexible straps 126 are spaced at intervals 132 along the rods 120, 124. The intervals 132 can be of equal space S between adjacent straps 126, the space S being approximately one inch to six inches. The smaller the space S between the flexible straps 126, the more precise and uniform the adjustments of the firmness/softness across the substrate 10 can be. The space S can vary between adjacent straps associated with different parts of the substrate 10. For example, the space S can be greater near the head and/or the foot of the substrate 10 than the space S between straps 126 supporting the substrate 10 approximate the torso and hip area of the subject 20.

The flexible straps 126 are made of a material that is strong enough so that it will not break under the weight of the substrate, subject and other items on the substrate. The material will flex, or stretch and contract due to changes in load determined by the width of the strap, the strap's elasticity or spring constant K and the spring's length or width. As non-limiting examples, the straps can be elastic, can be woven, braided or flat and can be polyester and/or rubber. Other examples of the material that may be used for the flexible straps 126 include silicone or metal wires. The flexible straps 126 can be between about 0.125 inch to 6 inches in width. The change in the elasticity of the strap changes the firmness. As the strap is stretched, the force required to return to the strap to a contracted state is non-linear, giving the supported mattress a different firmness. As with a guitar string, as the strap is tightened, the frequency changes.

The rods 120, 124 are a material that has sufficient strength to withstand the force of the total weight of the substrate 10, the subject 20 and other items on the substrate or the subject. As a non-limiting example, the rods 120, 124 are metal. The rods 120, 124 can be integral to the frame, separate from the frame, or can be used without a frame entirely. In embodiments in which the second rod 124 does not move, the second rod 124 can be eliminated and the end 128 of the strap 126 to directly attached to an anchor such as a portion of the bed frame 12 by fasteners such as staples or nails.

Figure 3A:
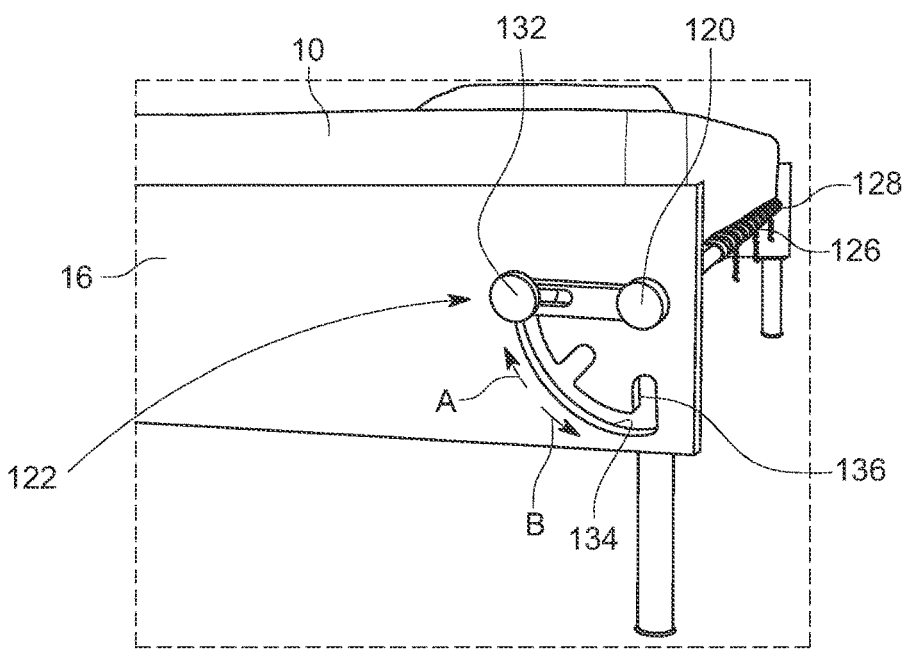
FIGS. 3A-3C illustrate an embodiment of a mechanism for adjusting the firmness of the substrate as disclosed herein.
Figure 3B:
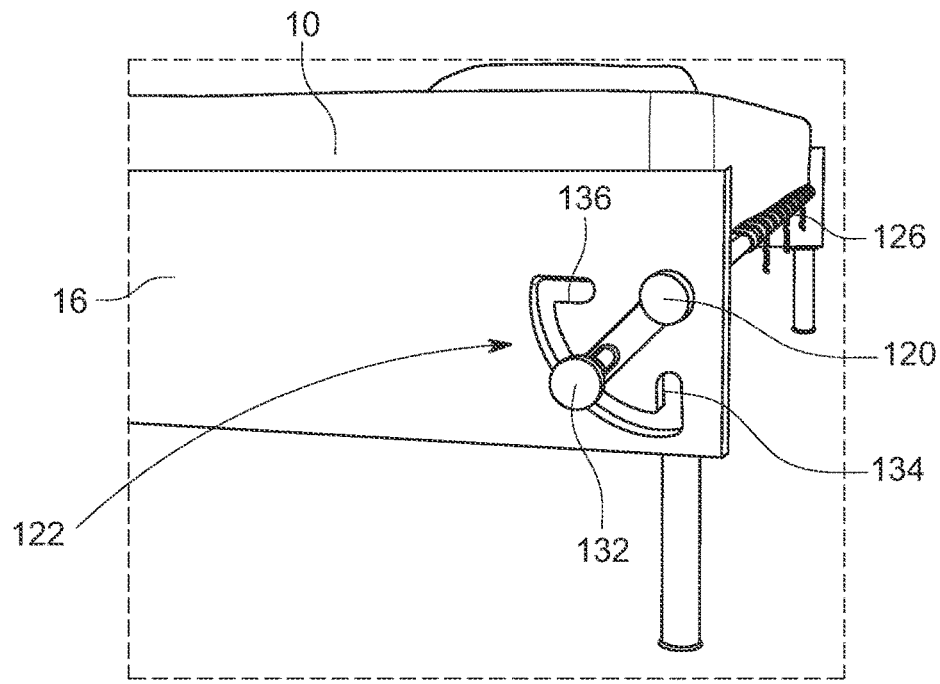
Figure 3C:
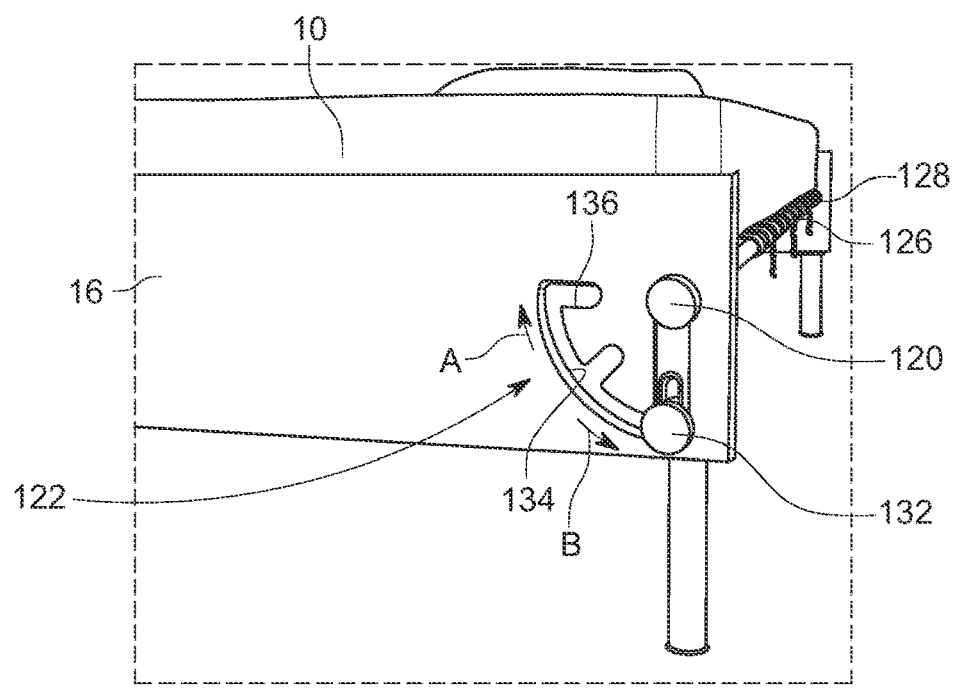

As illustrated in FIGS. 3A-3C, the mechanism 122 is configured to move, e.g., rotate, the first rod 120 in a first direction A to increase tension on the flexible straps 126 and move, e.g., rotate, the first rod 120 in a second direction B to decrease tension on the flexible straps 126. Note that the side board 14 is removed to show the end 128 of the straps 126. In FIG. 3A, the mechanism 122 is positioned such that the rod 120 is turned to the tightest position so that the flexible straps 126 are adjusted to the highest tension setting, resulting in the firmest substrate setting. In FIG. 3B, the mechanism 122 is positioned such that the rod 120 is turned to an intermediate position so that the flexible straps 126 have an intermediate tension resulting in an intermediate firmness. In FIG. 3C, the mechanism 122 is positioned such that the rod 120 is turned to a least tensioned position so the at the flexible straps 126 have the least tension resulting in a least firm substrate. The mechanism 122 illustrated in FIGS. 3A-3C is a non-limiting example. The mechanism 122 illustrated is manually operated by the subject 20 or another to adjust the tension of the flexible straps 126, in turn adjusting the firmness of the substrate 10, to that desired by the subject 20. The mechanism 122 has a handle 132 accessible to the subject 20 or another so that the handle 132 can be grasped and manually moved through a channel 134, the handle 132 turning the rod 120 as the handle 132 is moved through the channel 134. Multiple stops 136 are provided in which the handle 132 can be fixed to set the tension/firmness. The mechanism 122 can have fewer or more settings of adjustment as desired by changing the number of stops 136 and/or the distance the handle 132 travels and the rod 120 turns. However, the mechanism 122 can function in a different way so long as the result is the turning of a rod in two directions to change the tension on the flexible straps 126.

Figure 4:
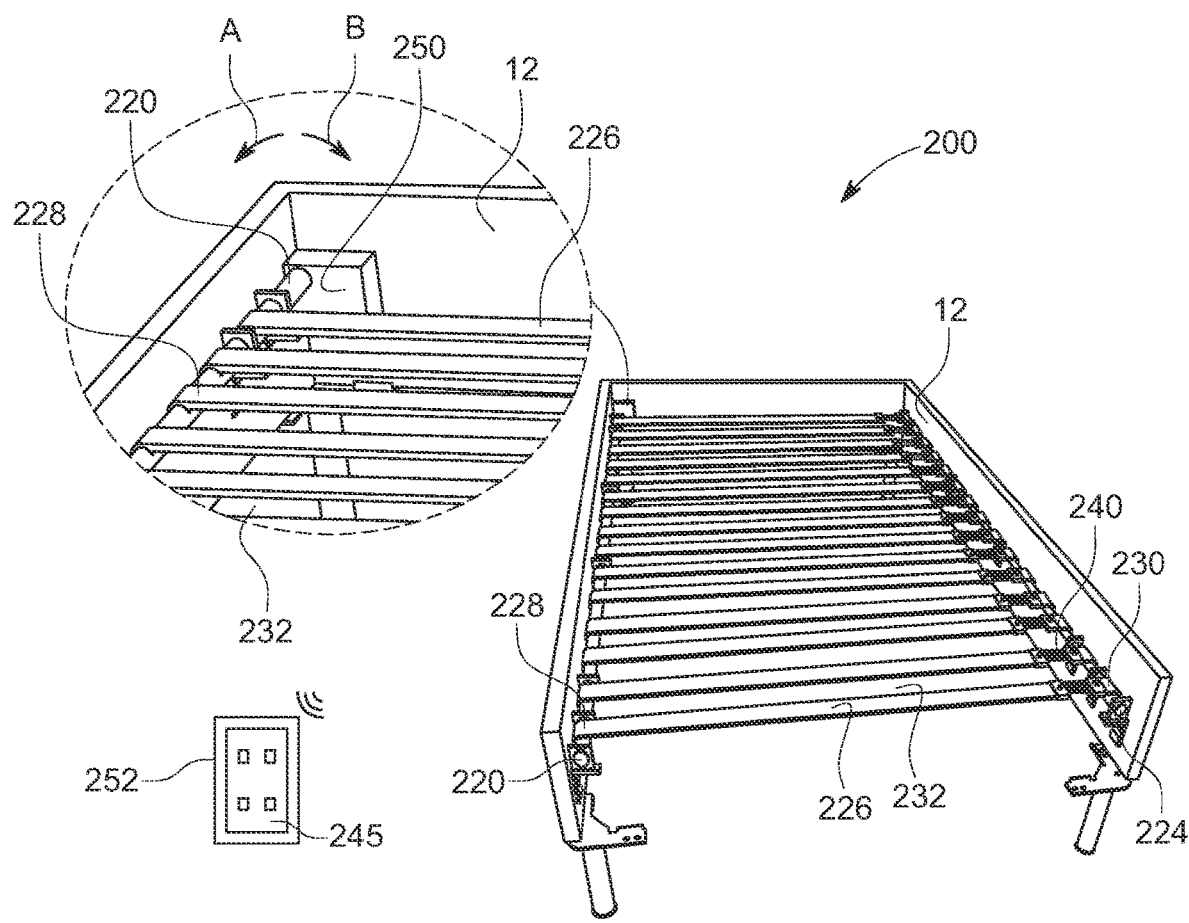
FIG. 4 is a perspective view of another embodiment of a system for adjusting the firmness of the substrate as disclosed herein.

FIG. 4 illustrates another embodiment of a system 200 for adjusting the firmness of a substrate 10 configured to support a subject 20. Similar to FIG. 2, FIG. 4 illustrates the system 200 when the substrate 10 is removed, exposing the system. The bed frame 12 illustrated is an example only. Like reference numbers will be used with like elements.

As in system 100, system 200 includes the first rod 220 configured to be movable and a second rod 224 parallel to and spaced from the first rod 220 a distance that spans a majority or an entirety of the width W of the substrate 10 and/or bed frame 12. Straps 226 extend between the first rod 220 and the second rod 224 and attach to the first rod 220 and the second rod 224 at respective ends 228, 230 of each strap 226. The rods 220, 224 extend along the frame 12 in a head-to-toe direction H with respect to a subject 20 lying on the substrate 10 as described with respect to system 100. Multiple flexible straps 226 are used so that when spaced along the parallel rods 220, 224, the flexible straps 226 extend along the entire length or a majority of the length of the rods 220, 224. The flexible straps 226 are spaced at intervals 232 along the rods 220, 224. The intervals 132 can be of equal space S between adjacent straps 126, the space S being approximately one inch to six inches. The smaller the space S between the flexible straps 126, the more precise and uniform the adjustments of the firmness/softness across the substrate 10 can be. The space S can vary between adjacent straps associated with different parts of the substrate 10. For example, the space S can be greater near the head and/or the foot of the substrate 10 than the space S between straps 126 supporting the substrate 10 approximate the torso and hip area of the subject 20.

Figure 5:
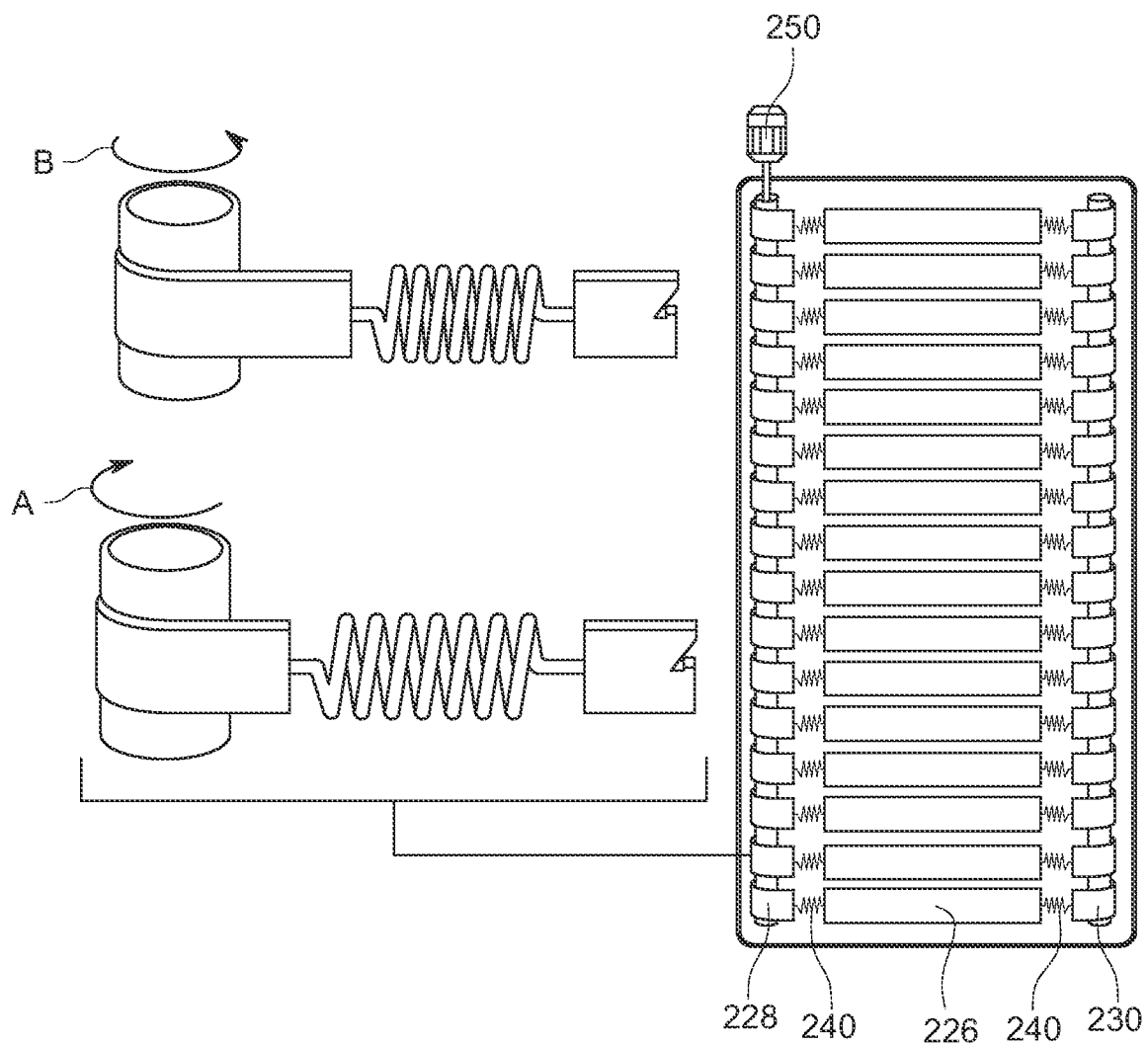
FIG. 5 is a plan view of a system for adjusting the firmness of the substrate, the system illustrating another aspect of flexible straps as disclosed herein.

Each flexible strap 226 can include a spring 240 proximate one end. As illustrated in FIG. 4, the spring 240 is proximate end 230. However, the spring 240 can be proximate end 228 instead. Alternatively, each strap 226 can include a spring 240 proximate each end as illustrated in FIG. 5 or can use the flexible straps 126 with no springs as described with respect to FIG. 2. Flexible straps 226 can be of a material that is not elastic as the springs 240 will provide the elasticity to the straps 226. The springs 240 are in series with the strap 226. As the tension increases, the springs 240 stretch or contract. As a spring's tension changes, the spring's K or spring constant acts according to Hookes Law. The difference in spring constant K makes the bed softer or stiffer. If there was no compliance in the straps or no use of springs, tightening the straps would just raise or lower the mattress.

Non-limiting examples of non-elastic strap material includes woven or flat nylon, polyester, polypropylene and cotton. Alternatively, the straps 226 can also be of an elastic material such as described with respect to system 100. The springs 240 and the elastic material together may allow for a larger number of settings with a broader range of firmness/softness. The flexible straps 226 of system 200 can be used with the manual mechanism 122 described with respect to system 100.

As shown in FIG. 4, system 200 includes a motor 250 as the mechanism to turn the rod 220 in the first direction A to increase tension on the flexible straps 226 and move the first rod 220 in the second direction B to decrease tension on the flexible straps 226. The motor 250 can run on a battery or can be plugged into a power outlet. The motor 250 can be operated by the subject 20 or another via a controller 252, which can receive an input from a user interface 254 through which the desired firmness is manually selected, such as by turning a knob to an indicated firmness setting or selecting on option on a touch screen panel. The controller 252 can be wired or wirelessly connected to the motor 250. The user interface 254 can be a display that is set on a night stand or can be an application on a mobile phone, as a non-limiting examples. The subject 20 can select a firmness setting through the user interface 254, which will communicate through the controller 252 with the motor 250 to adjust the rod 220 so that the desired firmness setting is achieved. The user interface 254 and the controller 252 can be an integrated unit or the user interface 254 can be separate from the controller but wired or wirelessly connected to the controller 252.

FIG. 5 illustrates another embodiment of a strap 326 having a spring 240 at each end 228, 230. This strap 326 can be used with either system 100 or system 200. FIG. 5 also illustrates the system 200 in plan view, illustrating the motor 250 along with how the motor 250 turns the rod to change the tension on the spring 250 and thus the strap 326.

Figure 6:
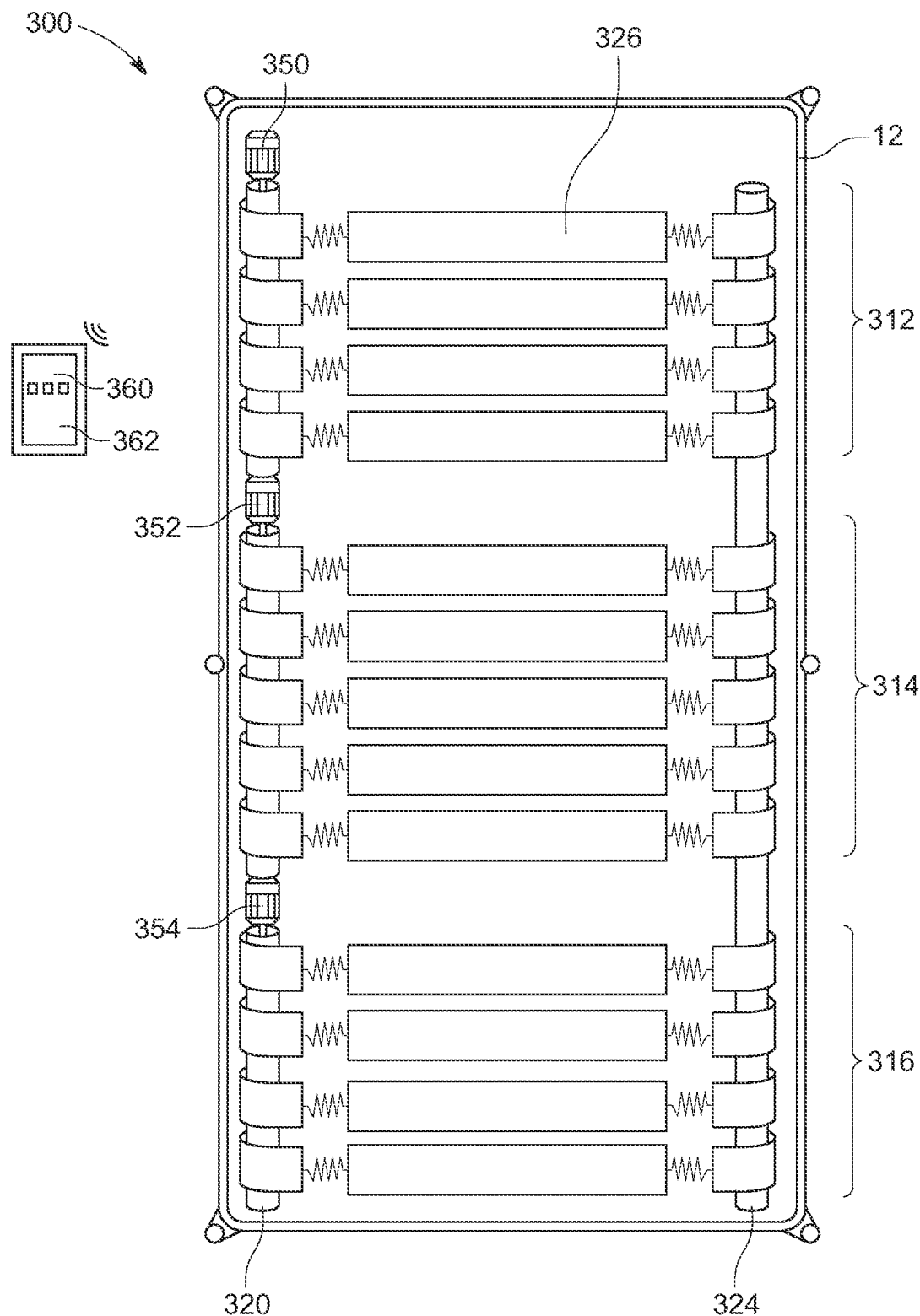
FIG. 6 is a plan view of another embodiment of a system for adjusting the firmness of the substrate as disclosed herein.

FIG. 6 illustrates another embodiment of a system 300 for adjusting the firmness of the substrate 10 configured to support the subject 20. In FIG. 6, the substrate 10 is removed so the system 300 can be seen in plan view. System 300 is shown using straps 326; however, system 300 can use flexible straps 126 or flexible straps 226 as desired. In system 300, the flexible straps 326 are divided into three groups, head section 310, mid-section 312 and foot section 314. Movable first rod 320 is also divided into three sections, each section operated by a respective motor 350, 352, 354.

Motor 350 operates the portion of movable rod 320 associated with the head section 310, motor 352 operates the portion of the movable rod 322 associated with the mid-section 312 and motor 354 operates the portion of the movable rod 324 associated with the foot section 314. The number of sections and motors is provided as illustration and is not meant to be limiting. The sections can have the same number of flexible straps 326 or can have different numbers of flexible straps 326. The different sections allow for different firmness results in different locations of the substrate. For example, the foot section 316 may be less firm than the mid-section 314. Each motor 350, 352, 354 moves its respective portion of the rod 320 in the first direction A to increase tension on the flexible straps 326 in the respective section and move the first rod 320 in the second direction B to decrease tension on the flexible straps 326. The motors 350, 352, 354 can run on batteries or can be plugged into a power outlet. The motors 350, 352, 354 can be operated by the subject 20 or another via a controller 360, which can receive an input from a user interface 362 through which the desired firmness for each section is manually selected, such as by turning a knob to an indicated firmness setting or selecting on option on a touch screen panel. The controller 360 can be wired or wirelessly connected to the motors 350, 352, 354. The user interface 362 can be a display that is set on a night stand or can be an application on a mobile phone, as non-limiting examples. The subject 20 can select firmness settings through the user interface 362, which will communicate through the controller 360 with the motors 350, 352, 354 to adjust the portions of the first rod 320 so that the desired firmness in each section is achieved. The user interface 362 and the controller 360 can be an integrated unit or the user interface 362 can be separate from the controller but wired or wirelessly connected to the controller 360.

Figure 7:
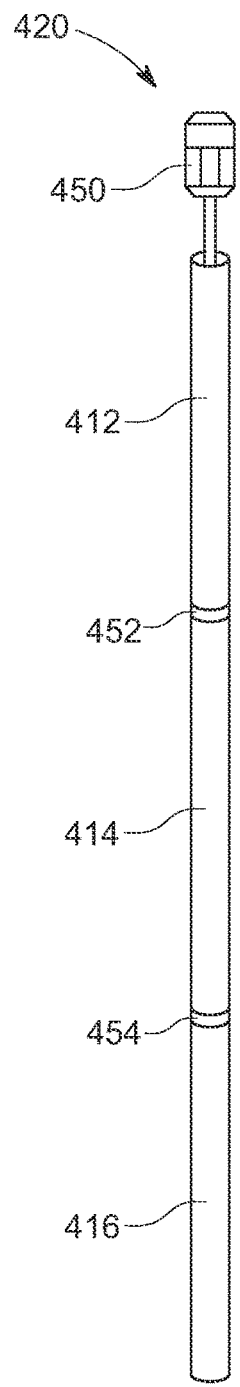
FIG. 7 illustrates an aspect of a movable rod used in embodiments of the system for adjusting the firmness of the substrate as disclosed herein.

FIG. 7 illustrates an alternative movable rod 420 and mechanism that can be used with system 300. In place of movable rod 320 and motors 350, 352, 354, movable rod 420 has sections 412, 414, 416 separated by clutches 452, 454. The controller 360 communicates with the motor 450 and the clutches 452, 454 to independently move the sections of the rod associated with the head section 312, the mid-section 314, and the foot section 316. In other words, motors 352 and 354 in system 300 are replaced with clutches 452 and 454.

Figure 8:
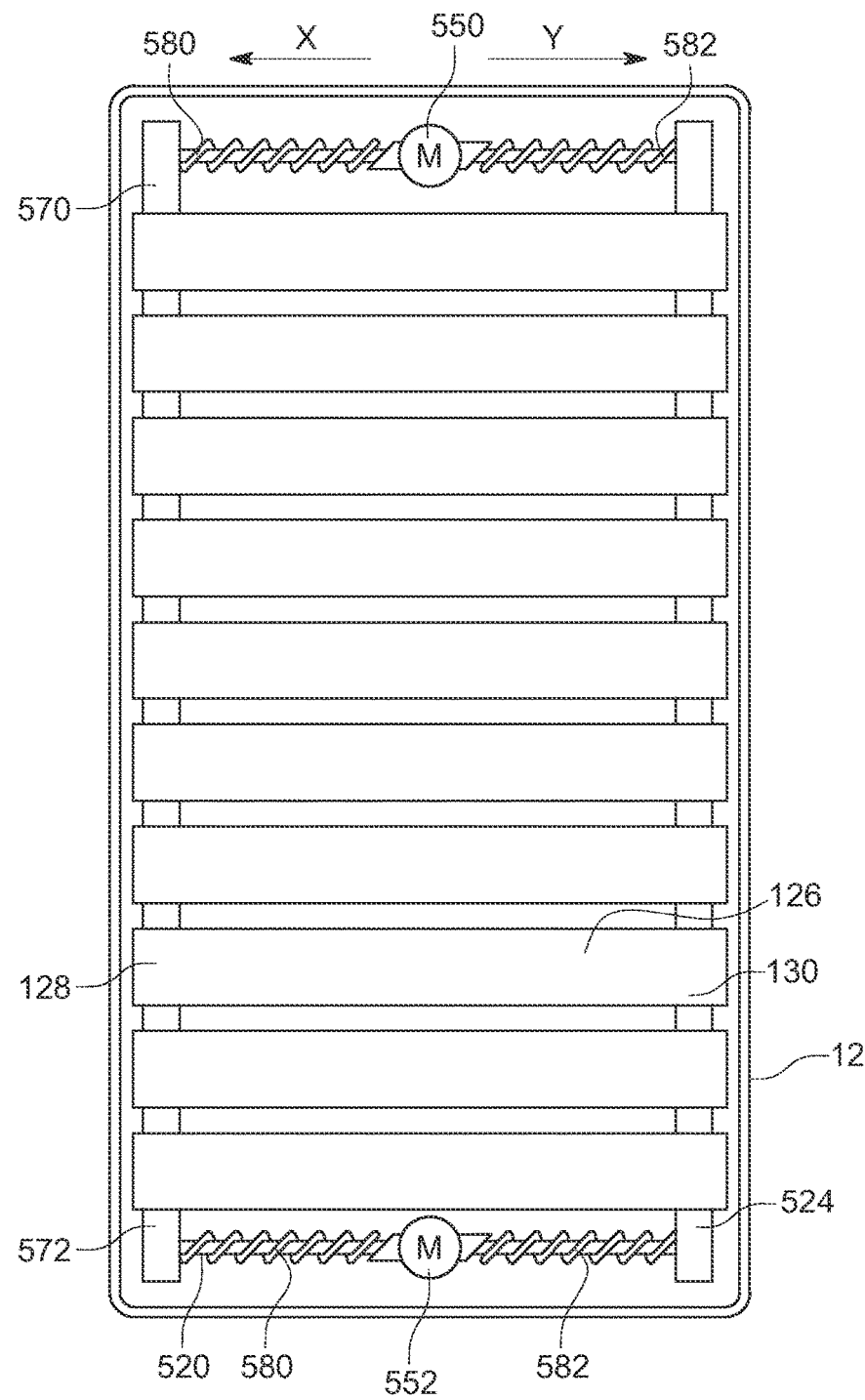
FIG. 8 is a plan view of another embodiment of a system for adjusting the firmness of the substrate as disclosed herein.

FIG. 8 illustrates another embodiment of a system 500 for adjusting the firmness of the substrate 10 configured to support the subject 20. The substrate 10 is removed in FIG.

8 and the system 500 is shown in plan view. System 500 is shown using straps 126, such as those in FIG. 1; however, system 500 can use flexible straps 226 or flexible straps 326 as desired.

In FIG. 8, both the first rod 520 and the second rod 524 are movable to adjust the tension of the flexible straps 126. The mechanism to move the rods 520, 524 includes a first motor 550 at one end 570 of the rods and a second motor 552 at the opposite end 572 of the rods. Each motor 550, 552 is configured to move the first rod 520 in a first direction X and the second rod 524 in an opposite second direction Y to increase the tension on the flexible straps 126. Each motor 550, 552 is also configured to move the first rod 520 in the second direction Y and the second rod 524 in the first direction X to decrease the tension on the flexible straps 126. The motors 550, 552 move the rods 520, 524 away from each other and closer to each other, rather than turning the rods. As a non-limiting example, motor 550 can turn an auger 580 in one direction that moves the rod 520 in the X direction and turn the auger 580 the opposite direction to move the rod 520 in the Y direction. Each motor 550, 552 would control two augers, one auger 580 connected to the first rod 520 and another auger 582 connected to the second rod 524. Other means of moving the rods 520, 524 with the motor in the X and Y directions that are within the knowledge of those skilled in the art are contemplated.

The motors 550, 552 in system 500 can be controlled by a controller and user interface as discussed with reference to systems 200, 300. Alternatively, the motors 550, 552 can be positioned such that motor 550 is configured to move, or rotate, the first rod 520 and motor 552 can be configured to move, or rotate, the second rod 524. Motor 550 can rotate first rod 520 in a first direction and motor 552 can rotate the second rod 524 in a second, opposite direction to tension the flexible straps. Motor 550 can rotate first rod 520 in the second direction and motor 552 can rotate the second rod 524 in the first direction to relax or contract the flexible straps.

Figure 9:
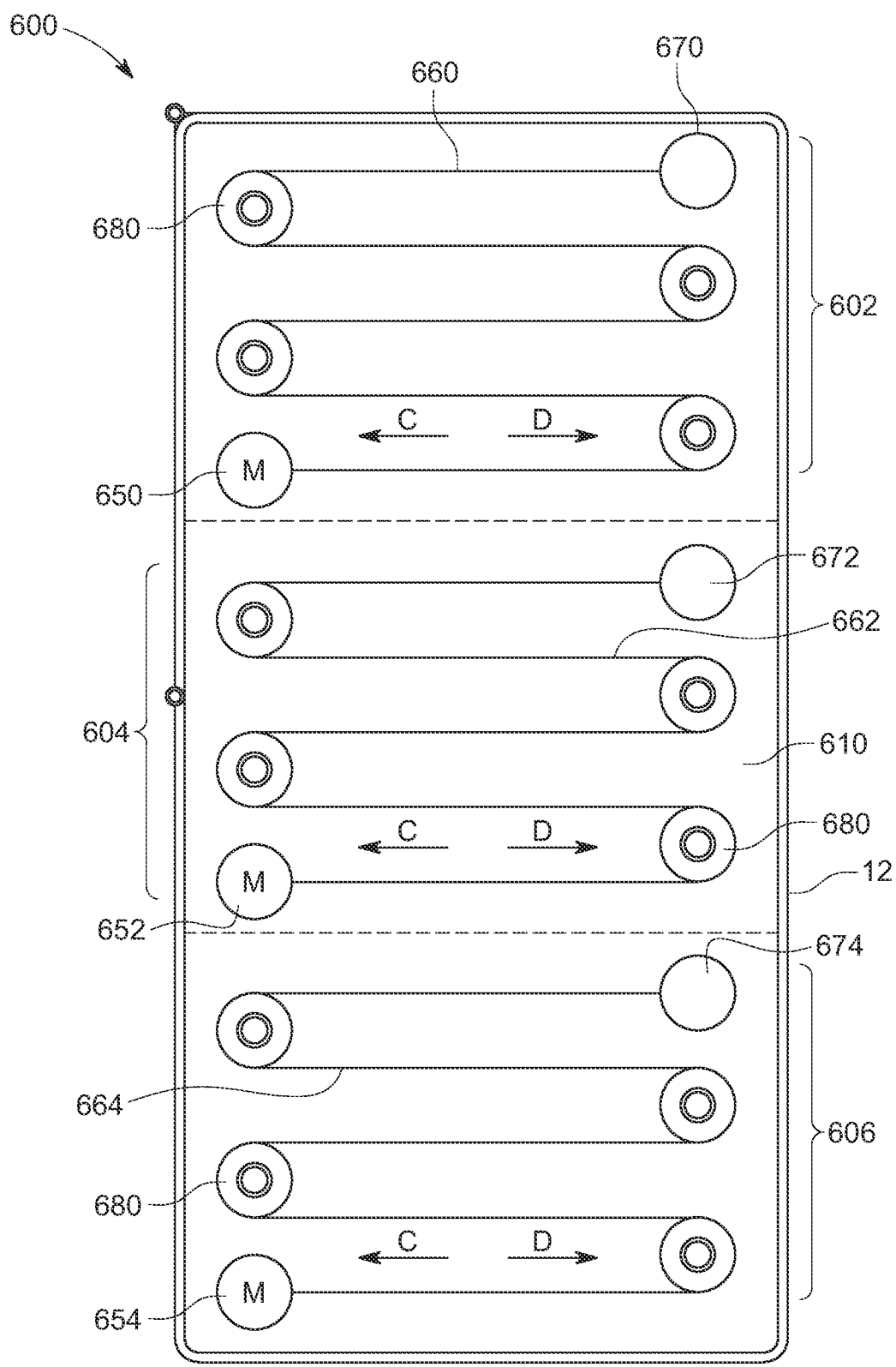
FIG. 9 is a plan view of another embodiment of a system for adjusting the firmness of the substrate as disclosed herein.

FIG. 9 illustrates another embodiment of a system 600 for adjusting the firmness of the substrate 10 configured to support the subject 20. The substrate 10 is removed in FIG. 9 and the system 600 is shown in plan view. In system 600, a pulley system is used to adjust tension on a cable. In FIG. 9, the area of the substrate and/or the bed frame is divided into three sections, a head section 602, mid-section 604 and a foot section 606. The division is provided as an example. The area can be divided in two sections or in more than three sections. The sections can be of equal areas or can be of different areas. Alternatively, the area is not divided, using only a single motor/cable.

A base 610 is positioned within the bed frame 12 and configured to be spaced from the substrate 10. The base 610 supports a motor in each section, motor 650 in head section 602, motor 652 in mid-section 604, and motor 654 in foot section 606. Each motor 650, 652, 654 is attached to a respective cable 660, 662, 664, which extends between the motor and a fixed member 670, 672, 674. Pulleys 680 are positioned as illustrated such that the cables 660, 662, 664 span a majority of the width of the substrate and/or bed frame. The number of pulleys 680 used in a section in FIG. 9 is provided as an example, with larger numbers of pulleys decreasing the cable spacing in the head-to-toe direction H. The base 610 is positioned within the bed frame 12 such than when the substrate 10 is supported, the substrate lies against the cables 660, 662, 664.

Firmness of the substrate 10 is adjusted by adjusting the tension on the cables 660, 662, 664. For example, motor 650 can wind the cable 660 in a first direction C such that the tension on the cable 660 is increased. This will increase the firmness of the substrate. Motor 650 can unwind the cable 660 in a second direction D such that the tension on the cable 660 is decreased, decreasing the firmness of the substrate.

The different sections allow for different firmness results in different locations of the substrate. For example, the foot section 606 may be less firm than the mid-section 604. The motors 650, 652, 654 in system 600 can be individually and selectively controlled by a controller and user interface as discussed with reference to systems 200, 300.

In each of the systems using a motor, the addition of a strain gauge on each flexible strap can add a higher level of automation and control of the firmness settings of the substrate. Any of the embodiments of the straps disclosed herein can incorporate a strain gauge.

Figure 10:
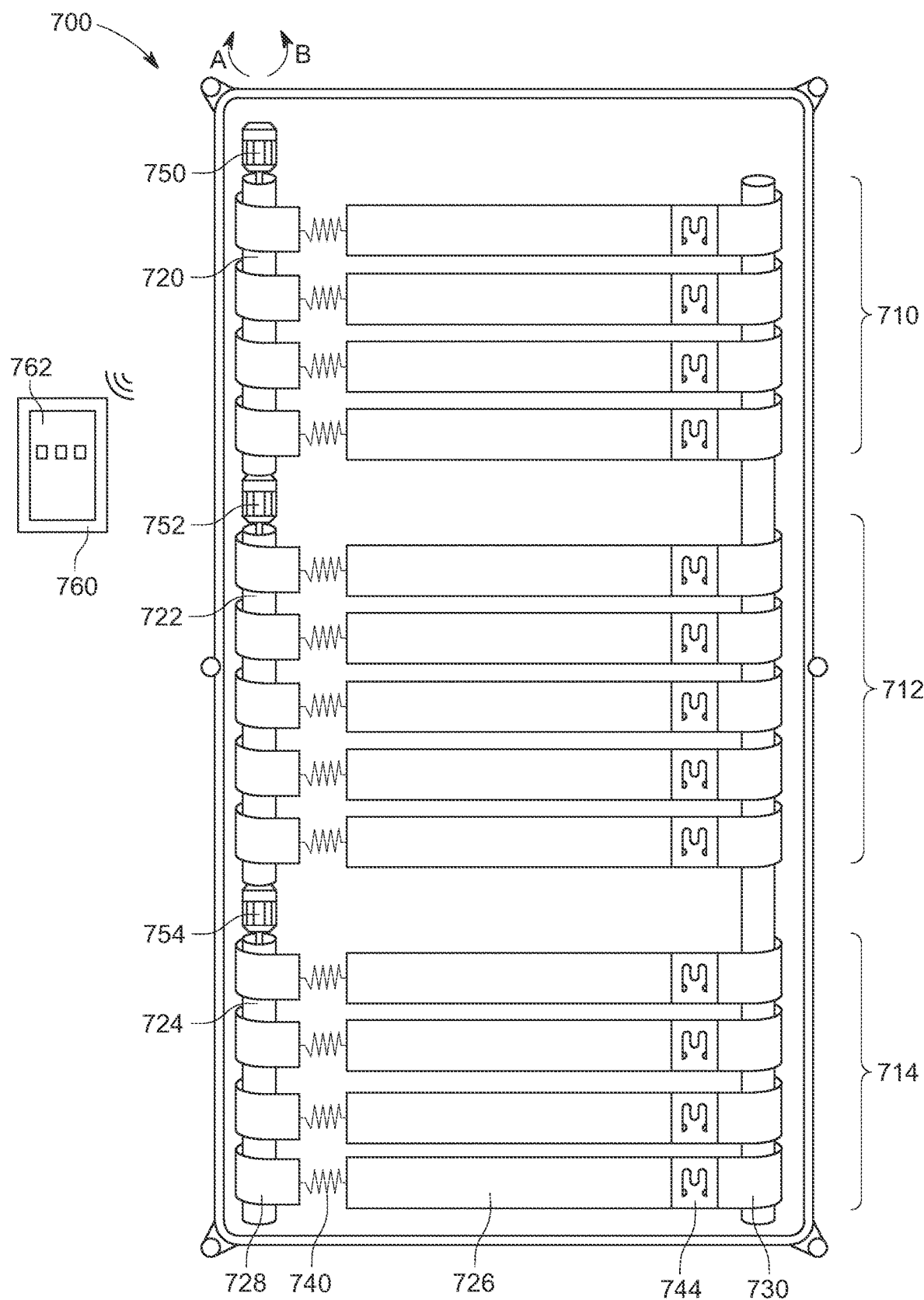
FIG. 10 is a plan view of another embodiment of a system for adjusting the firmness of the substrate as disclosed herein.

FIG. 10 illustrates a system 700 for adjusting the firmness of the substrate 10 configured to support the subject 20. In FIG. 10, the substrate 10 is removed so the system 700 can be seen in plan view. System 700 is shown using straps 726; however, system 700 can use flexible straps with no springs and made from flexible material or flexible straps with two springs as desired. Each flexible strap 726 includes a spring 740 proximate one end. As illustrated in FIG. 10, the spring 740 is proximate end 728. However, the spring 740 can be proximate end 730 instead. Each flexible strap 726 also includes a strain gauge 744 located proximate end 730. However, the strain gauge 744 can be located anywhere on the strap 726 such that it can measure the strain on the flexible strap or flexible strap and spring. Any kind of strain gauge can be used, such as linear, rosette, bull bridge, half bridge, as non-limiting examples. The strain gauge can be a load sensor or any other sensor that can measure the strain or tension on the flexible straps. Power to the strain gauges 744 can be provided from a power outlet or battery, as examples.

In system 700, the flexible straps 726 are divided into three groups, head section 710, mid-section 712 and foot section 714. Movable first rod is also divided into three sections, each section operated by a respective motor 750, 752, 754. Motor 750 operates the portion of movable rod 720 associated with the head section 710, motor 752 operates the portion of the movable rod 722 associated with the mid-section 712 and motor 754 operates the portion of the movable rod 724 associated with the foot section 714. The number of sections and motors is provided as illustration and is not meant to be limiting. The sections can have the same number of flexible straps 726 or can have different numbers of flexible straps 726. The different sections allow for different firmness results in different locations of the substrate. For example, the foot section 716 may be less firm than the mid-section 714. Each motor 750, 752, 754 moves its respective portion of the rod 720, 722, 724 in the first direction A to increase tension on the flexible straps 726 in the respective section and move the respective rod 720, 722, 724 in the second direction B to decrease tension on the flexible straps 726.

The motors 750, 752, 754 can run on batteries or can be plugged into a power outlet, for example. A controller 760 can operate the motors 750, 752, 754 to selectively adjust the tension on the flexible straps 726 in each section 710, 712, 714. The controller 760 can receive input from each of the strain gauges 744 and can operate the motors based on the input from each of the strain gauges 744 and/or user input via a user interface 762. As one example, a subject can input into the user interface 762 a different desired firmness setting for each of the head section 710, the mid-section 712 and the foot section 714. Each firmness setting will be associated with a level of strain on the flexible straps 726. The controller 760 will receive input from the strain gauges 744, distinguishing between the strain gauges 744 in each of the three sections. Based on the desired firmness and the firmness associated with the current strain gauge readings, the controller 760 can operate a motor 750, 752, 754 as required to adjust the firmness setting for a particular section to meet the desired firmness setting inputted by the subject. For example, the controller 760 may control motor 752 to increase the firmness of the mid-section 712 to meet the subject's desired firmness setting. The motor 752 would move the rod 722 in the A direction until the desired firmness is met based on the output from the strain gauges 744 in the mid-section 712. When the subject rolls onto his or her side, for example, the firmness level automatically increases based on the sleep position. The controller 760 will receive input from the strain gauges 744 that the firmness exceeds the subject's desired level of firmness and will control the motor 752 to move the rod 722 in the B direction until the strain gauges 744 in the mid-section 712 indicate the firmness has been decreased to the desired setting.

The controller 760 can be wired or wirelessly connected to the motors 750, 752, 754. The user interface 762 can be a display that is set on a night stand or can be an application on a mobile phone, as non-limiting examples. The user interface 762 and the controller 760 can be an integrated unit or the user interface 762 can be separate from the controller but wired or wirelessly connected to the controller 760.

Figure 11:
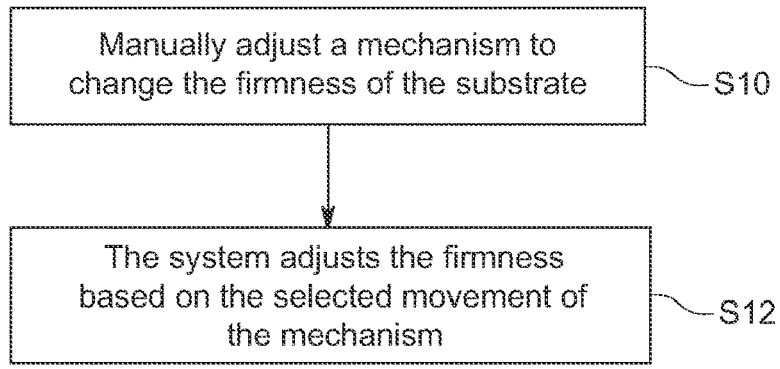
FIG. 11 is a flow diagram of a method of adjusting the firmness of the substrate using the systems disclosed herein.

Methods of controlling the firmness of a substrate are also disclosed herein. In one method, illustrated in FIG. 11, a subject manually adjusts a mechanism to change the firmness of the substrate in step 10. In step 12, the mechanism simultaneously turns a rod in one of a first direction to increase the firmness or a second direction to decrease the firmness.

Figure 12:
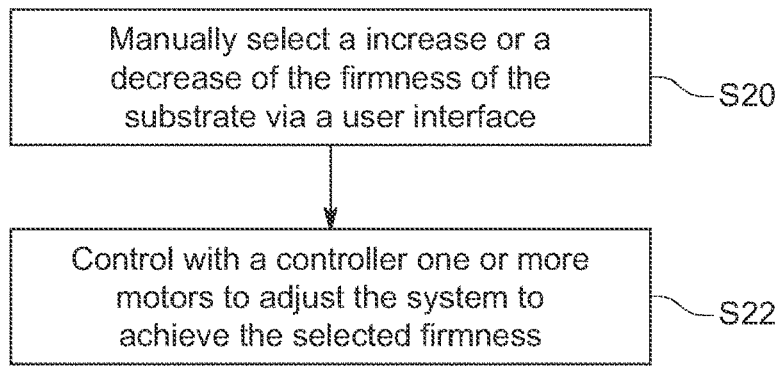
FIG. 12 is a flow diagram of another method of adjusting the firmness of the substrate using the systems disclosed herein.

In another method, illustrated in FIG. 12, the subject manually selects an increase or a decrease of the firmness of the substrate via a user interface in step 20. In step 22, a controller directs one or more motors to adjust the system in response to the subject's input. The system that is adjusted may be any of the systems disclosed herein.

Figure 13:
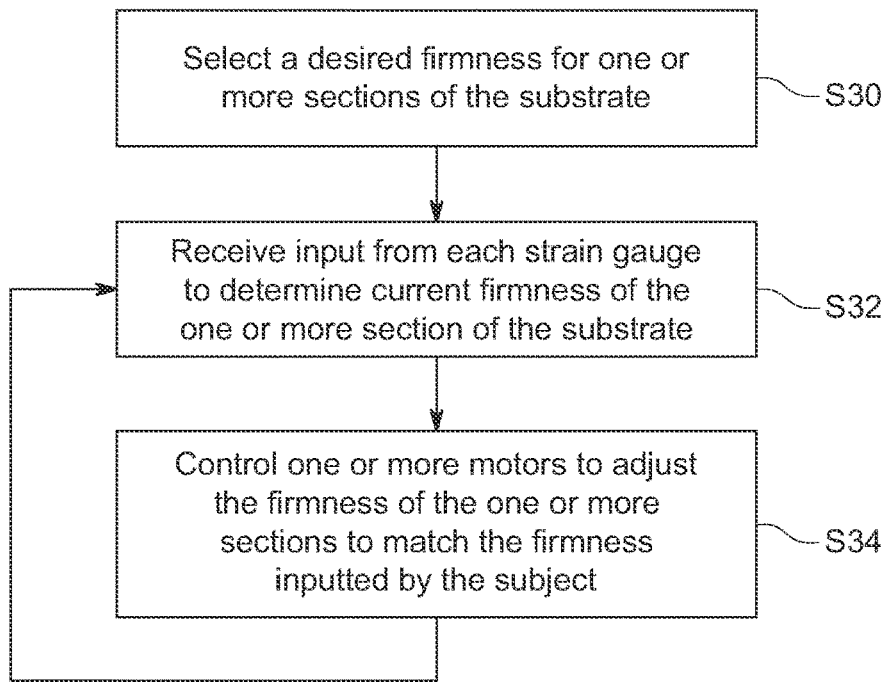
FIG. 13 is a flow diagram of another method of adjusting the firmness of the substrate using the systems disclosed herein.

In another method, illustrated in FIG. 13, the subject selects a desired firmness for one or more sections of the substrate in step 30. When the subject lies on the substrate, in step 32, the controller receives input from each strain gauge associated with a respective flexible strap and determines the firmness of the one or more sections of the substrate. In step 34, the controller controls one or more motors to adjust the firmness of the one or more sections to match the firmness inputted by the subject. The controller continuously receives input from the strain gauges and controls the one or more motors in real time to maintain the desired firmness, the one or more motors adjusting the one or more sections as the strain measured by the strain gauges change. The strain will change based on the position of the subject, such as whether the subject is on his or her back, side or stomach, as non-limiting examples.

The systems herein are illustrated with a single bed. However, the systems herein can be used in any size bed. For example, in a queen or king size bed intended to support two subjects, two systems would be used side-by-side so that each system could be selectively and individually controlled.

The systems herein are illustrated with a mattress and bed frame, the mattress and bed frame being utilized in any location, such as home, medical facility or hotel. But the figures are not meant to be limiting. The systems herein can be used with other substrates on which a subject rests, including but not limited to a bed with no side frame, a chair, a hospital bed, a support in a doctor's office or other medical facility, the seat of an automobile, train or plane, a sofa bed and a couch.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A system for adjusting firmness of a substrate configured to support a subject, the system comprising:
    a first rod configured to be movable by a mechanism, the first rod positioned proximate a lateral edge of the substrate;
    flexible straps extending between the first rod and an anchor and attached to the first rod and the anchor at respective ends of each flexible strap, the anchor positioned proximate an opposing lateral edge of the substrate, the anchor being one of a second rod and a frame portion configured to support the substrate; and
    a second rod as the anchor, the second rod parallel to and spaced from the first rod a distance that spans a majority of a dimension of the substrate, wherein the flexible straps extend between the first rod and the second rod, and wherein the second rod is also configured to be movable by the mechanism, the mechanism configured to:
    move the first rod in a first direction and the second rod in a second direction to increase tension on the flexible straps; and
    move the first rod in a second direction and the second rod in the first direction to decrease tension on the flexible straps.

2. The system of claim 1, wherein the mechanism is a handle extending from the first rod to be accessible to the subject, the handle movable by the subject to rotate the first rod in the first direction and rotate the first rod in the second direction, the mechanism including stops to hold the handle in a particular position, the particular position associated with a selected firmness.

3. The system of claim 1, wherein each flexible strap comprises a central portion, a first rod attachment portion, and a second anchor attachment portion, with a spring connecting the central portion to one of the first rod attachment portion and the second anchor attachment portion.

4. The system of claim 1, wherein the mechanism is a motor, the system further comprising a controller configured to control the motor.

5. The system of claim 4, wherein the controller is further configured to receive input from the subject directing an increase or a decrease in the firmness of the substrate, the controller controlling the motor to move the first rod based on the input.

6. The system of claim 4, further comprising:
    strain gauges, each strain gauge associated with a respective flexible strap and configured to measure a strain on the respective flexible strap and output the strain to the controller.

7. The system of claim 6, wherein the first rod has multiple sections each configured to move independently from other sections via clutches, each clutch associated with a respective section, and wherein the controller is further configured to control the motor to selectively individually move each of the multiple sections based on the strain outputted by each strain gauge.

8. The system of claim 6, wherein the first rod has multiple sections and the motor is multiple motors, each of the multiple sections configured to move independently from other sections via an associated motor.

9. The system of claim 8, wherein the controller is further configured to control each of the multiple motors to selectively individually move each of the multiple sections based on the strain outputted by each strain gauge.

10. The system of claim 1, and further comprising means to select a firmness setting and communicate through a controller.

11. The system of claim 1, wherein the mechanism is further configured to move the first rod and move the second rod to adjust the firmness of a portion of the substrate.

12. A system for adjusting firmness of a substrate configured to support a subject, the system comprising:
a motor;
a controller configured to control the motor;
a first rod configured to be moved by the motor;
a second rod parallel to the first rod, the first rod and the second rod spaced to span a majority of a width of the substrate;
flexible straps extending between the first rod and the second rod and attached to the first rod and the second rod at respective ends of each flexible strap; and
strain gauges, each strain gauge associated with a respective flexible strap and configured to measure a strain on the respective flexible strap and output the strain to the controller, wherein in the controller is configured to control the motor to:
move the first rod in a first direction to increase tension on the flexible straps; and
move the first rod in a second direction to decrease tension on the flexible straps,
wherein the first rod has multiple sections and the motor is multiple motors, each of the multiple sections configured to move independently from other sections via an associated motor.

13. The system of claim 12, wherein the controller is further configured to receive input from the subject directing an increase or a decrease in the firmness of the substrate, the controller controlling at least one of the multiple motors the motor based on the input.

14. The system of claim 12, wherein each flexible strap comprises a central portion, a first rod attachment portion, and a second rod attachment portion, with a spring connecting the central portion to one of the first rod attachment portion and the second rod attachment portion.

15. The system of claim 12, wherein at least one of the multiple motors moves the first rod away from the second rod when the controller moves the first rod in the first direction to increase tension on the flexible straps and moves the first rod toward the second rod when the controller moves the first rod in the second direction to decrease tension on the flexible straps.

16. The system of claim 15, wherein the second rod is also configured to be moved by the motor, the controller further configured to control the motor to:
move the second rod away from the first rod to increase tension on the flexible straps and move the second rod toward the first rod to decrease tension on the flexible straps.

17. The system of claim 12, wherein the controller is further configured to control each of the multiple motors to selectively individually move each of the multiple sections based on the strain outputted by each strain gauge.

18. The system of claim 12, and further comprising means to select a firmness setting and communicate through the controller.

19. The system of claim 12, wherein at least one of the multiple motors are aligned axially along a centerline axis of the first rod.

20. A system for adjusting firmness of a substrate configured to support a subject, the system comprising:
a motor;
a controller configured to control the motor;
a first rod configured to be moved by the motor;
a second rod parallel to the first rod, the first rod and the second rod spaced to span a majority of a width of the substrate;
flexible straps extending between the first rod and the second rod and attached to the first rod and the second rod at respective ends of each flexible strap; and
strain gauges, each strain gauge associated with a respective flexible strap and configured to measure a strain on the respective flexible strap and output the strain to the controller, wherein in the controller is configured to control the motor to:
move the first rod in a first direction to increase tension on the flexible straps; and
move the first rod in a second direction to decrease tension on the flexible straps, wherein the first rod has multiple sections each configured to move independently from other sections via clutches, each clutch associated with a respective section.

21. The system of claim 20, wherein the controller is further configured to control the motor to selectively individually move each of the multiple sections based on the strain outputted by each strain gauge.

22. The system of claim 20, and further comprising means to select a firmness setting and communicate through the controller.

* * * * *